(12) United States Patent
Covert et al.

(10) Patent No.: US 7,807,875 B2
(45) Date of Patent: Oct. 5, 2010

(54) DROUGHT AND HIGH LIGHT TOLERANT TRANSGENIC PLANTS

(75) Inventors: Sarah F. Covert, Athens, GA (US); Terri A. Long, Durham, NC (US); Gregory W. Schmidt, Bishop, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 201 days.

(21) Appl. No.: 11/507,766

(22) Filed: Aug. 22, 2006

(65) Prior Publication Data

US 2008/0216195 A1 Sep. 4, 2008

Related U.S. Application Data

(60) Provisional application No. 60/710,307, filed on Aug. 22, 2005.

(51) Int. Cl.
*C12N 15/82* (2006.01)
*A01H 5/00* (2006.01)

(52) U.S. Cl. .................. 800/289; 800/298; 435/419; 435/468

(58) Field of Classification Search ................. None
See application file for complete search history.

(56) References Cited

U.S. PATENT DOCUMENTS 6,239,332 B1* 5/2001 Ko et al. ............... 800/290
2005/0026280 A1 2/2005 Tasaka

OTHER PUBLICATIONS

Munekage Y. et al. PGR5 Is Involved in Cyclic Electron Flow around Photosystem I and is essential for Photoprotection in Arabidopsis. Cell, Aug. 9, 2002, vol. 110, pp. 361-371.*
Yabuta Y. et al. Thylakoid membrane-bound ascorbate peroxidase is a limiting factor of antioxidative systems under photo-oxidative stress. The Plant Journal 2002, vol. 32, pp. 915-925.*
Long T.A. et al. Conserved role of Proton Gradient Regulation 5 in the regulation of PSI cyclic electron transport. Planta. Jul. 29, 2008. [Epub ahead of print].*
Jefferson R.A. et al. GUS fusions: beta-glucuronidase as a sensitive and versatile gene fusion marker in higher plants. EMBO J. Dec. 20, 1987;6(13):3901-7.*
International Search Report and Written Opinion, dated Jul. 28, 2008.
Munekage, T., et al. "PGR5 is Involved in Cyclic Electron Flow Around Photosystem I and is Essential for Photoprotection in Arabidopsis" Cell. Aug. 9, 2002, vol. 110, pp. 361-371.
Yabuta, Y., et al. "Thyllakoid Membrane-Bound Ascorbate Peroxidave is a Limiting Factor of Antioxidative Systems Under Photo-Oxidative Stress" The Plant Journal, 2002, vol. 32, pp. 915-925.
Cyclic Electron Flow Around Photosystem I is Essential for Photosynthesis, Munekage, Y., et al., Nature, vol. 429, Jun. 3, 2004, pp. 579-582.
PGR5 Is Involved in Cyclic Electron Flow around Photosystem I and Is Essential for Photoprotection in Arabidopsis, Munekage, Y., et al., Cell, vol. 110, Aug. 9, 2002, pp. 361-371.
Differential Expression of Pine and Cronartium Quercuum f. sp. fusiforme Genes in Fusiform Rust Galls, Warren, et al., Applied and Environmental Microbiology, vol. 70, No. 1, Jan. 2004, pp. 441-451.
Cyclic Electron Transport in C3 plants: fact or artefact?, Johnson, G., Journal of Experimental Botany, vol. 56, No. 411, Jan. 2005, pp. 407-416.
Differential Use of Two Cyclic Electron Flows Around Photosystem I for driving Co2-Concentration Mechanism in C4 Photosynthesis, Takabayashi, A., et al., PNAS, vol. 102, No. 46, Nov. 2005, pp. 16898-16903.
Open Reading Frame ssr2015 is Required for Antimycin A-sensitive Photosystem I-driven Cyclic Electron Flow in the Cyanobacterium *Synechocystis* sp. PCC 6803, Yeremenko, N., et al. Plant Cell Physiol. 46(8): 2005, pp. 1433-1436.
Regulating the Proton Budget of Higher Plant Phogosynthesis, Avenson, T., et al., PNAS, vol. 102, No. 27, Jul. 2005, pp. 9709-9713.

* cited by examiner

*Primary Examiner*—Cynthia Collins
(74) *Attorney, Agent, or Firm*—Thomas, Kayden, Horstemeyer & Risley, LLP

(57) ABSTRACT

Transformed plants and/or plant cells having increased tolerance to high light, drought, water-deficit, and/or other stress-inducing conditions are provided. Plants and plant cells expressing or over-expressing an exogenous nucleic acid encoding a polypeptide involved in a CET pathway, including but not limited to, a PGR5 polypeptide, and methods of making the transformed plants and plant cells are also provided.

39 Claims, 9 Drawing Sheets

Figure 7

SEQ ID NO: 1

ATCTGTTACAGATTATTACTGTACAATCCAGCAAAAACT
AGGCCTGGGATTTCGGATTAACCCAATGACCGAACTG
                                             DRECRTCOREAT
AACAAACCGTTTTTTGGTTCTGATAACCGACTATGAA
AACACOREOSGLUB1             GATABOX
GGGAAGGCTAAACCGATCGGCGAAATTATAATTGAAGT
TCGGTTCTCGGTTCGGCAGACATAACCGATCAGTTTTCT
CGGTTAATAGATACTATAAATATAAAGATAAAAACAT
  GTICORE  GATABOX          GATABOX
TAGATCTAATCTTTTAGCTTCTTCTCCGTTTCCTTTTGA
                                        PYRIMIDINEBOXOSRAMY1A
TCCTCATCCATGGCTATTTAGTCAATTCTCTCTATCTGC
ATGTGGTTTTCACTATGGTAGCACGTCGGGGCATATTT
                            ACGTATERD1
CGTTACGGAGATATCGTCATCCCTCGCTATCACCGTCAC
         GATABOX
CGTCACAGACGTAGATCTGCTGATTATGAAGAGGGTAGC
        ACGTATERD1
GGCACCAAGATACCATCAACCCTAATTTTTAATAGGT
        GATABOX
TTGGATTTTTAGTTATTTTGGGTTTAAGTTTGTTTTTCGTTTT
GGCCCAATTATTGGTTTGTAATTATAAAATTTTGTT
TATCTTCGCCCATTCTATAATTTTTGTTTTGACCCATTATCTT
                                ELRECOREPCRP1
GATTTTGGACTTATTCGGTATAAACTAACCGAACT
AAAAAAAAAATCGGTTTAGTTCAGAGTTGATTTTGAATCCT
       DRECRTCOREAT
ATAACCAAACCGACCCGAACCAAATCTTTATTCGG
REALPHALGLHCB12     REALPHALGLHCB12
TTTAATTTGACAAAATTTTAAAGAACCGAAAAACC
                            LTRE1HVBLT49
GATTAAACCAAACCGAACCGATTACCCGAATAAACCGAA
TGCCCAGGCCAAAAACAACTGAAAATAAAAAATAAAAAAT
GAGATAGGAGAATATTTAATCCGACGGTGGAGAAA
  GATABOX                      DRE1COREZMRAB17  POLLEN1LELAT52
                          GTGANTG10
TGTTGATATAATAAAACGTGATACAGAGGATCATAAACCC
      GATABOX   ACGTATERD1  GATABOX
GCAACATGAGAAACGTAATAAGTTAAGTCAAAAA
              ACGTATERD1
AACGAAAAAGCCAGAATCATATTTGTGGCTCTGGTTTCTC
CATCCAAACAAAAACAACACCCAAACCTTGTCCACA
CCAAAATGTTAAACTCAAAATCCAACCACACACACAATT
TCTCTTCCTCTCTACCATTAACATCGATCAGAAAG
                                  POLLEN1LELAT52
ACCGAGAGAGAGGGAGAAGCTGATTGATT
DRE1COREZMRAB17

DROUGHT AND HIGH LIGHT TOLERANT TRANSGENIC PLANTS

CROSS-REFERENCE TO RELATED APPLICATION

This application claims priority to copending U.S. provisional patent application Ser. No. 60/710,307, entitled "Drought and High Light Tolerant Transgenic Plants" filed on Aug. 22, 2005, which is entirely incorporated herein by reference.

STATEMENT REGARDING FEDERALLY SPONSORED RESEARCH OR DEVELOPMENT

This application has received Federal Government Support by NSF Agency, Grant Nos. DGE-9616054 and OCE-0137007; NIH Agency, Grant No. GM07103; and McIntire Stennis Cooperative Forestry Act, Grant Nos. GEO-0119-MS and GEO-0887-MS. The government has certain rights in the invention.

BACKGROUND

Environmental stressors, such as drought, water-deficit, high light, and extreme temperatures, represent a few of the major factors that affect plant growth, survival, and productivity. Droughts, transfer of plants from greenhouse to field, and extreme temperature and light fluctuations can be devastating to crop and ornamental plants, resulting in the loss of billions of dollars. Breeding of stress-tolerant crops is one approach to these problems, but conventional breeding is a slow process for generating plant varieties with improved tolerance to stress conditions. Limited germplasm resources for stress tolerance and incompatibility in crosses between distantly related plant species are additional problems encountered in conventional breeding. Recent progress in plant genetic transformation and the availability of potentially useful genes characterized from different sources have made it possible to generate stress-tolerant crops using transgenic approaches.

In most photosynthetic organisms, the conversion of light energy to chemical energy occurs largely through linear electron transport (LET), which generates both the NADPH and the ATP required for $CO_2$ assimilation. However, electrons can also transfer cyclically around PSI from ferredoxin (Fd) or NADPH back to the plastoquinone pool (PQ), thus generating ATP via cyclic electron transport (CET). In cyanobacteria, green algae, and the bundle sheath cells of $C_4$ plants, CET can be the exclusive source of photosynthetically-derived ATP, or it can act to provide extra ATP for different cellular processes. In $C_3$ plants, the importance of CET has been the subject of much debate; it has been proposed to play a key role in photoprotection by mediating nonphotochemical quenching (NPQ) and stromal redox status, and alternatively to generate ATP essential for the Calvin Cycle and other metabolic processes.

Two CET pathways are known to exist in $C_3$ plants. In one of them, electron transfer from Fd to PQ requires proton gradient regulation 5 (PGR5). PGR5 is a small, nucleus-encoded, thylakoid membrane-associated protein. Research suggests that PGR5-dependent CET acts to increase thylakoid lumen pH ($\Delta$pH) under photoinhibitory conditions by facilitating the movement of electrons from NADPH or Fd to the PQ pool (Munekage et al., 2002). In the second CET pathway, electron transfer from NADPH to the PQ pool is mediated by NAD(P)H dehydrogenase (NDH). NDH is a large, partly chloroplast-encoded, thylakoid membrane-bound, multi-subunit complex. Research suggests that the two CET pathways act in a partially redundant manner to generate the ATP needed for proper growth (Munekage et al., 2004).

SUMMARY

Briefly described, embodiments of this disclosure provide transformed plants and/or plant cells having increased tolerance to high light, drought, water-deficit and/or other stress-inducing conditions, including, but not limited to, extreme temperatures, physical damage, and high salinity, by virtue of expressing or over-expressing an exogenous nucleic acid (e.g., a gene or gene fragment) encoding a polypeptide involved in a CET pathway, including, but not limited to, a PGR5 polypeptide, as compared to wild type plants not expressing the exogenous nucleic acid. Embodiments of the present disclosure also provide methods of making the transformed plants and plant cells described above.

In some exemplary embodiments of the present disclosure, transformed plant cells are provided that include a recombinant nucleic acid sequence including an exogenous nucleic acid encoding a PGR5 polypeptide. Expression of the exogenous PGR5 nucleic acid increases the tolerance of the cell to high light, drought, water-deficit and/or other stress-inducing conditions. Expression of the exogenous PGR5 nucleic acid increases the activity of PGR5-dependent cyclic electron transport in the transformed plant cell.

A transformed plant cell according to the present disclosure can be cultivated to generate a transgenic plant. Embodiments of the present disclosure also include transgenic plants whose genome includes a recombinant nucleic acid including an exogenous nucleic acid encoding a PGR5 polypeptide, where expression of the PGR5 nucleic acid increases the tolerance of the plant to high light, drought, water-deficit, and/or other stress-inducing conditions.

In various embodiments, the transformed plants and/or plant cells of the present disclosure also include a nucleic acid encoding a gene expression promoter operably linked to the exogenous nucleic acid sequence encoding for a PGR5 polypeptide. In various embodiments, the promoter may be a constitutive or stress-inducible promoter and may induce over-expression of the exogenous nucleic acid. In other embodiments, the transformed plants and/or plant cells also include a nucleic acid sequence encoding a selectable marker.

Embodiments of the present disclosure also include methods of producing a transgenic plant and/or plant cell having increased tolerance to high light, water-deficit, drought, and/or other stress-inducing conditions. Such embodiments include introducing into a plant cell a recombinant nucleic acid sequence that includes an exogenous nucleic acid encoding a PGR5 polypeptide and expressing the PGR5 polypeptide in the cell. Embodiments also include cultivating a transgenic plant cell, as provided above, and cultivating the cell to generate a plant.

The details of some embodiments of the present disclosure are set forth in the description below. Other features, objects, and advantages of the present disclosure will be apparent to one of skill in the art upon examination of the following description, drawings, examples and claims. It is intended that all such additional systems, methods, features, and advantages be included within this description, be within the scope of the present disclosure, and be protected by the accompanying claims.

BRIEF DESCRIPTION OF THE DRAWINGS

The disclosure can be better understood with reference to the following drawings. The components in the drawings are not necessarily to scale, emphasis instead being placed upon clearly illustrating the principles of the present disclosure.

FIG. 1A is a northern blot of WT and two AtPGR5 RNAi lines, Ri5 and Ri9; the RNAi lines have loss of PGR5 expression via RNA interference. FIG. 1B illustrates immunodetection of AtPGR5 in WT, Ri5, and Ri9. FIG. 1C is a northern blot of WT and an AtPGR5 over-expression line, AtOE20. FIG. 1D illustrates immunodetection of AtPGR5 in WT and AtOE20. FIG. 1F is a northern blot of WT and PtOE17. Northern blots were probed with AtPGR5 (FIGS. 1A and 1C) or PtPGR5 (FIG. 1F). The bottom panels in FIGS. 1A, 1C, and 1F show ethidium bromide staining of the corresponding RNA gel to demonstrate equivalent messenger RNA sample loads in the analyses. The bottom panels in FIGS. 1B and 1D show Coomassie blue staining of a corresponding protein gel to demonstrate equivalent amounts of protein extracts in the analyses.

FIG. 2A is a graph of PSII yield ($f_{PSII}$). FIG. 2B is a graph of the electron transport rate (ETR) through PSII, and FIG. 2C illustrates the nonphotochemical quenching (NPQ) of chlorophyll fluorescence. Means±SE (n=2-5).

FIG. 3A illustrates two week old wild-type (WT) and AtPGR5 RNAi (Ri5) plants germinated and grown under high intensity light (2000 μE/m$^2$s). FIG. 3B shows the leaves from 2-week-old WT and Ri5 plants grown in sealed boxes under moderate intensity light (150 μE/m$^2$s). FIG. 3C shows the leaves from 3A treated with NBT (nitroblue tetrazolium) to detect superoxide anion levels.

FIG. 5A shows four-week-old plants grown in moderate light, then shifted to high intensity light for four days. FIG. 5B shows seven-week-old plants grown under moderate light for 4 weeks, then shifted to high light (HL) for 3 weeks. FIG. 5C illustrates six-week-old plants three weeks after cessation of water application, grown at constant high light (2000 light μE/m$^2$s).

FIG. 6A shows expression in four-day-old seedlings grown under no light and under constant light. FIGS. 6B-6D illustrate expression patterns in a two-week-old whole plant (6B), a four-week-old whole plant (6C), and a five-week-old whole plant (6D). FIGS. 6E and 6F depict expression in a cross-section of stem primary vascular tissue (6E), and in a cross-section of stem secondary vascular tissue (6F). FIG. 6G illustrates expression patterns in germinating seed. FIG. 6H shows expression in the seed coat remaining after embryo emergence. FIG. 6I shows expression patterns in floral tissues, and FIG. 6J illustrates expression in fully expanded leaves from five week old plants at three time points post wounding (PW).

FIG. 7 is a sequence listing of the ATPRG5 regulatory region (SEQ. ID NO: 1) (−1100 kb to −1) showing putative cis regulatory elements (underlined or over-lined) in the regulatory region that are assumed to regulate PGR5 gene expression. Pollen-specific elements: POLLEN1LELAT52, and GTGANTG10; etiolation-specific elements: ABRELATERD1, ACGTATERD1, and REALPHALGLHCB21; endosperm-specific element: CACOREOSGLUB1; wound-specific element: ELRECOREPCRP1; light-specific elements (double underlined), GATABOX, and IBOXCORE; cold-specific elements: LTRECOREATCOR15, and LTRE1HVBLT49; drought regulatory elements: DRE1COREZMRAB17, and DRECRTCOREAT; and a sucrose repression element: PYRIMIDINEBOXOSRAMY1A.

FIG. 8A shows AtPGR5 transcript levels after 0, 1, 3, 6, or 12 hrs exposure to high light (2000 μE/m$^2$s), and FIG. 8B shows AtPGR5 transcript levels after 0, 1, or 3 days of chilling at 4° C. The bottom row in each panel shows the corresponding RNA gel stained with ethidium bromide.

DETAILED DESCRIPTION

Figure 1:
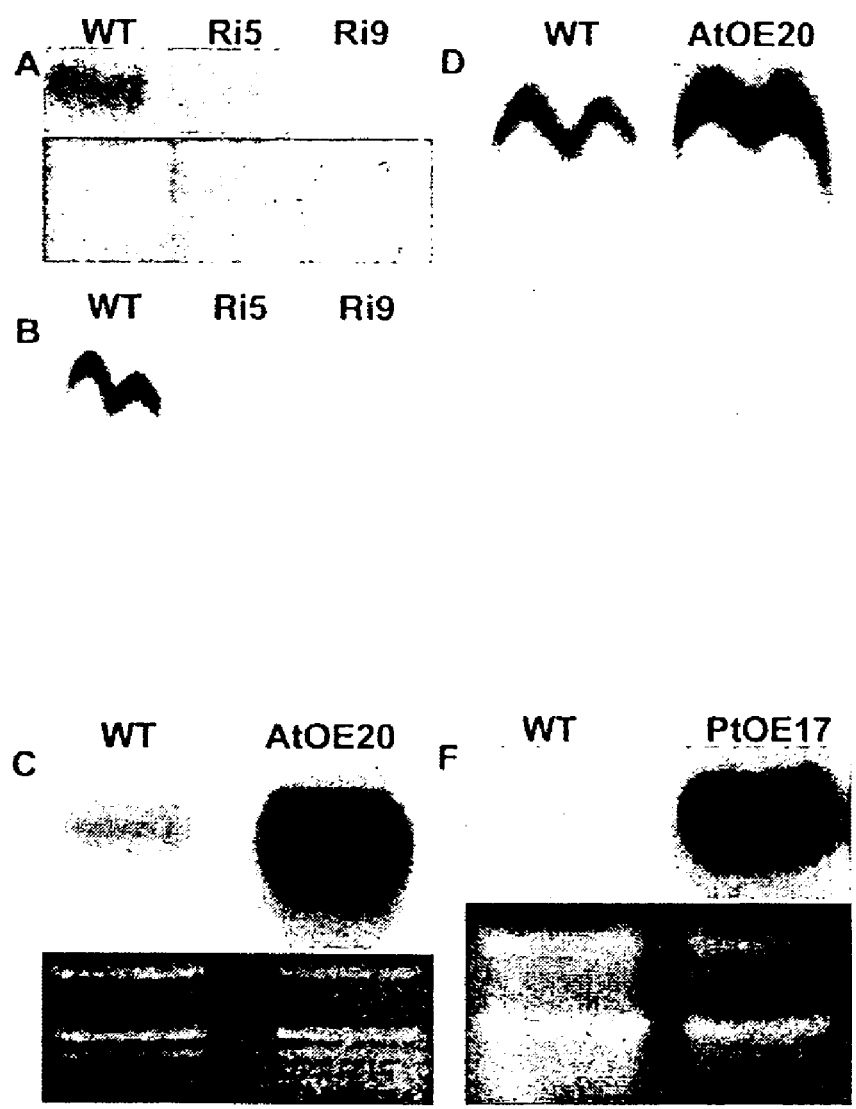
FIGS. 1A through 1F illustrate PGR5 expression in wild-type (WT) and transgenic Arabidopsis thaliana leaves.

Embodiments of the present disclosure will employ, unless otherwise indicated, conventional techniques of synthetic organic chemistry, biochemistry, molecular biology, and the like, which are within the skill of one in the art. Such techniques are explained fully in the literature.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

The following examples are put forth so as to provide those of ordinary skill in the art with a complete disclosure and description of how to perform the methods and use the compositions disclosed and claimed herein. Efforts have been made to ensure accuracy with respect to numbers (e.g., amounts, temperature, etc.) but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that unless otherwise indicated the present disclosure is not limited to particular materials, reagents, reaction materials, manufacturing processes, or the like, as such may vary. It is also to be understood that the terminology used herein is for purposes of describing particular embodiments only, and is not intended to be limiting. It is also possible in the present disclosure that steps may be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Prior to describing the various embodiments, the following definitions are provided and should be used unless otherwise indicated.

Definitions:

In describing and claiming the disclosed subject matter, the following terminology will be used in accordance with the definitions set forth below.

In accordance with the present disclosure there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual" (1982); "DNA Cloning: A Practical Approach," Volumes I and II (D. N. Glover ed. 1985); "Oligonucleotide Synthesis" (M. J. Gait ed. 1984); "Nucleic Acid Hybridization" (B. D. Hames & S. J. Higgins eds. (1985)); and "Transcription and Translation" (B. D. Hames & S. J. Higgins eds. (1984)).

As used herein, the term "PGR5" refers to a proton gradient regulation 5 polypeptide (e.g., a PGR5 protein, active fragment thereof, functional variant thereof, or homolog thereof) or nucleic acid (e.g., a PGR5 gene, or fragment or homolog thereof that encodes a PGR5 polypeptide, as defined herein) from a plant (e.g., *Arabidopsis thaliana*), or any homologous polypeptide or nucleic acid from a plant or other organism.

The terms "nucleic acid" and "polynucleotide" are terms that generally refer to a string of at least two base-sugar-phosphate combinations. As used herein, the terms include deoxyribonucleic acid (DNA) and ribonucleic acid (RNA) and generally refer to any polyribonucleotide or polydeoxribonucleotide, which may be unmodified RNA or DNA or modified RNA or DNA. RNA may be in the form of a tRNA (transfer RNA), snRNA (small nuclear RNA), rRNA (ribosomal RNA), mRNA (messenger RNA), anti-sense RNA, RNAi (RNA interference construct), siRNA (short interfering RNA), or ribozymes. Thus, for instance, polynucleotides as used herein refers to, among others, single-and double-stranded DNA, DNA that is a mixture of single-and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. The terms "nucleic acid sequence" and "oligonucleotide" also encompasses a nucleic acid and polynucleotide as defined above.

In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia.

For instance, the term polynucleotide includes DNAs or RNAs as described above that contain one or more modified bases. Thus, DNAs or RNAs comprising unusual bases, such as inosine, or modified bases, such as tritylated bases, to name just two examples, are polynucleotides as the term is used herein.

The term also includes PNAs (peptide nucleic acids), phosphorothioates, and other variants of the phosphate backbone of native nucleic acids. Natural nucleic acids have a phosphate backbone, artificial nucleic acids may contain other types of backbones, but contain the same bases. Thus, DNAs or RNAs with backbones modified for stability or for other reasons are "nucleic acids" or "polynucleotides" as that term is intended herein. A "gene" typically refers to the portion(s) of a nucleic acid that encode a protein/polypeptide.

As used herein, the term "exogenous DNA" or "exogenous nucleic acid sequence" or "exogenous polynucleotide" refers to a nucleic acid sequence that was introduced into a cell, organism, or organelle via transfection. Exogenous nucleic acids originate from an external source, for instance, the exogenous nucleic acid may be from another cell or organism and/or it may be synthetic and/or recombinant. While an exogenous nucleic acid sometimes originates from a different organism or species, it may also originate from the same species (e.g., an extra copy or recombinant form of a nucleic acid that is introduced into a cell or organism in addition to or as a replacement for the naturally occurring nucleic acid). Typically, the introduced exogenous sequence is a recombinant sequence.

As used herein, the term "transfection" refers to the introduction of an exogenous nucleic acid sequence into the interior of a membrane enclosed space of a living cell, including introduction of the nucleic acid sequence into the cytosol of a cell as well as the interior space of a mitochondria, nucleus, or chloroplast. The nucleic acid may be in the form of naked DNA or RNA, it may be associated with various proteins or regulatory elements (e.g., a promoter and/or signal element), or the nucleic acid may be incorporated into a vector or a chromosome. A "transformed" cell is thus a cell transfected with a nucleic acid sequence. The term "transformation" refers to the introduction of a nucleic acid (e.g., DNA or RNA) into cells in such a way as to allow expression of the coding portions of the introduced nucleic acid. The term "transgene" refers to an artificial gene which is used to transform a cell of an organism, such as a bacterium or a plant.

The term "recombinant" generally refers to a non-naturally occurring nucleic acid, nucleic acid construct, or polypeptide. Such non-naturally occurring nucleic acids include natural nucleic acids that have been modified, for example that have deletions, substitutions, inversions, insertions, etc., and combinations of nucleic acid sequences of different origin that are joined using molecular biology technologies (e.g., a nucleic acid sequences encoding a "fusion protein" (e.g, a protein or polypeptide formed from the combination of two different proteins or protein fragments), the combination of a nucleic acid encoding a polypeptide to a promoter sequence, where the coding sequence and promoter sequence are from different sources or otherwise do not typically occur together naturally). Recombinant also refers to the polypeptide encoded by the recombinant nucleic acid. Non-naturally occurring nucleic acids or polypeptides include nucleic acids and polypeptides modified by man.

The term "polypeptides" and "protein" include proteins and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

"Variant" refers to a polypeptide that differs from a reference polypeptide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally. In addition, the term "variant" as used herein includes circular permutations of proteins and peptides.

Modifications and changes can be made in the structure of the polypeptides of disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly, where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of interest.

As used herein "functional variant" refers to a variant of a protein or polypeptide (e.g., a variant of a PGR5 protein) that can perform the same functions or activities as the original protein or polypeptide, although not necessarily at the same level (e.g., the variant may have enhanced, reduced or changed functionality, so long as it retains the basic function).

"Identity," as known in the art, is a relationship between two or more polypeptide sequences, as determined by comparing the sequences. In the art, "identity" also refers to the degree of sequence relatedness between polypeptides as determined by the match between strings of such sequences. "Identity" and "similarity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M, and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J Applied Math., 48: 1073 (1988).

Preferred methods to determine identity are designed to give the largest match between the sequences tested. Methods to determine identity and similarity are codified in publicly available computer programs. The percent identity between two sequences can be determined by using analysis software (e.g., Sequence Analysis Software Package of the Genetics Computer Group, Madison Wis.) that incorporates the Needelman and Wunsch, (J. Mol. Biol., 48: 443-453, 1970) algorithm (e.g., NBLAST, and XBLAST). The default parameters are used to determine the identity for the polypeptides of the present disclosure.

By way of example, a polypeptide sequence may be identical to the reference sequence, that is be 100% identical, or it may include up to a certain integer number of amino acid alterations as compared to the reference sequence such that the % identity is less than 100%. Such alterations are selected from: at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in the reference polypeptide by the numerical percent of the respective percent identity (divided by 100) and then subtracting that product from said total number of amino acids in the reference polypeptide.

As used herein, the term "tolerant" or "tolerance" refers to the ability of a plant to overcome, completely or to some degree, the detrimental effect of an environmental stress or other limiting factor. In embodiments of the present disclosure, the transgenic plants are tolerant to conditions including, but not limited to, high light conditions, water-deficit, drought conditions (e.g., prolonged and/or extreme water-deficit), and/or other stress inducing conditions by virtue of producing an abundance of PGR5.

The term "expression" as used herein describes the process undergone by a structural gene to produce a polypeptide. It is a combination of transcription and translation. Expression generally refers to the "expression" of a nucleic acid to produce a polypeptide, but it is also generally acceptable to refer to "expression" of a polypeptide, indicating that the polypeptide is being produced via expression of the corresponding nucleic acid.

As used herein, the term "over-expression" refers to the expression of a nucleic acid encoding a polypeptide (e.g., a gene) in a transformed plant cell at higher levels (therefore producing an increased amount of the polypeptide encoded by the gene) than the "wild type" plant cell (e.g., a substantially equivalent cell that is not transfected with the gene) under substantially similar conditions. Thus, to over-express or increase expression of a PGR5 nucleic acid refers to increasing or inducing the production of the PGR5 polypeptide encoded by the nucleic acid, which may be done by a variety of approaches, such as increasing the number of genes encoding for the polypeptide, increasing the transcription of the gene (such as by placing the gene under the control of a constitutive promoter), or increasing the translation of the gene, or a combination of these and/or other approaches.

The term "plasmid" as used herein refers to a non-chromosomal double-stranded DNA sequence including an intact "replicon" such that the plasmid is replicated in a host cell.

As used herein, the term "vector" or "expression vector" is used in reference to a vehicle used to introduce an exogenous nucleic acid sequence into a cell. A vector may include a DNA molecule, linear or circular, which includes a segment encoding a polypeptide of interest operably linked to additional segments that provide for its transcription and translation upon introduction into a host cell or host cell organelles. Such additional segments may include promoter and terminator sequences, and may also include one or more origins of replication, one or more selectable markers, an enhancer, a polyadenylation signal, etc. Expression vectors are generally derived from yeast or bacterial genomic or plasmid DNA, or viral DNA, or may contain elements of both.

As used herein, the term "promoter" or "promoter region" includes all sequences capable of driving transcription of a coding sequence. In particular, the term "promoter" as used herein refers to a DNA sequence generally described as the 5' regulator region of a gene, located proximal to the start codon. The transcription of an adjacent coding sequence(s) is initiated at the promoter region. The term "promoter" also includes fragments of a promoter that are functional in initiating transcription of the gene.

The term "operably linked" indicates that the regulatory sequences necessary for expression of the coding sequences of a nucleic acid are placed in the nucleic acid molecule in the appropriate positions relative to the coding sequence so as to effect expression of the coding sequence. This same definition is sometimes applied to the arrangement of coding sequences and transcription control elements (e.g. promoters, enhancers, and termination elements), and/or selectable markers in an expression vector.

As used herein, the term "selectable marker" refers to a gene whose expression allows one to identify cells that have been transformed or transfected with a vector containing the marker gene. For instance, a recombinant nucleic acid may include a selectable marker operably linked to a gene of interest and a promoter, such that expression of the selectable marker indicates the successful transformation of the cell with the gene of interest.

As used herein, the term "high light" refers to environmental conditions where the amount of natural and/or artificial light is greater than the average light conditions for the particular environment, or the amount of light exceeds, on average, the natural light tolerance range of a plant growing in that environment.

As used herein, the terms "drought" and "water-deficit" refer to environmental conditions where the amount of water (e.g., rainfall or other available water source for plant life) is less than the average water conditions for the particular environment, or the amount of water available is less than the amount of water typically needed by a certain species of plant or by a plant growing in a particular environment. Typically a "drought" indicates a more intense or more prolonged period of reduced water availability than a "water-deficit".

As used herein "low temperatures" indicates that the temperatures in an environment are lower than the average temperatures for a particular environment and/or for a particular season. In addition, "low temperatures" refers to temperatures that are lower than a range of temperatures typically tolerated by a particular plant species.

As used herein "wounding" refers to any physical damage or injury inflicted on a plant or plant cell. Such physical damage may be inflicted manually/physically or chemically or by any other method resulting in a physical injury to the plant or cell.

Having defined some of the terms herein, the various embodiments of the disclosure will be described.

Description:

Embodiments of the present disclosure include a transformed plant cell including a recombinant nucleic acid that includes an exogenous PGR5 nucleic acid (e.g., a PGR5 gene or fragment thereof) encoding a PGR5 polypeptide. The nucleic acid could be RNA or DNA, preferably cDNA, and can be biologically isolated or synthetic. Expression or over-expression of the PGR5 nucleic acid (e.g., driven by a stress-inducible or constitutive promoter) increases tolerance of the cell to environmental stresses including, but not limited to, high light, drought, water-deficit, wounding and/or low temperatures. Exemplary PGR5 homologues useful for the transgenic plants of the present disclosure include, for example, AtPGR5 (derived from *Arabidopsis thaliana*) (SEQ ID NO: 2 (nucleotide) and SEQ ID NO: 3 (protein)) and PtPGR5 (derived from *Pinus taeda*) (SEQ ID NO: 4 (nucleotide) and SEQ ID NO: 5 (protein)). The plant cell to be transfected can be any plant cell, including, but not limited to, a dicot plant cell (e.g., a tomato cell, a brassica cell (e.g., *A. thaliana*), a potato cell, and the like), a monocot plant cell (e.g., a rice cell, a wheat cell, a barley cell, and the like), or a gymnosperm cell (e.g., a pine cell, a spruce cell, a gingko cell and the like).

In some embodiments, over-expression of PGR5 is induced pursuant to the present disclosure in food crop plants in order to confer tolerance to drought, water-deficit, high light and other extreme environmental conditions that could devastate such crops, resulting in shortages of important food sources. In other embodiments of the present disclosure, regularly light-sensitive plants (e.g., ornamental shade plants and seedlings of most plants) are transfected with exogenous PGR5 to confer greater light tolerance. For instance, a plant genetically altered pursuant to this disclosure that had been raised in a green-house or shade-house could be directly transferred to full-sun without damage. This is significant, as photoacclimation of greenhouse-propagated seedlings is a major problem in ornamental and culinary plant enterprises.

While some embodiments of nucleotide sequences referred to herein encode a PGR5 polypeptide, nucleotide identity to a previously sequenced PGR5 gene is not required. As should be readily apparent to those skilled in the art, various nucleotide substitutions are possible that are silent mutations (e.g., the amino acid encoded by the particular codon does not change). It is also possible to substitute a nucleotide that alters the amino acid encoded by a particular codon, where the amino acid substituted is a conservative substitution (e.g., amino acid "homology" is conserved). It is also possible to have minor nucleotide and/or amino acid additions, deletions, and/or substitutions in the PGR5 protein nucleotide and/or amino acid sequences that have minimal influence on the properties, secondary structure, and hydrophilic/hydrophobic nature of the encoded PGR5 protein. These variants are encompassed by the nucleic acid encoding a PGR5 protein according to the subject disclosure.

Also encompassed by the present disclosure are transgenic plants transformed with fragments of the nucleic acids encoding the PGR5 proteins of the present disclosure. Suitable fragments capable of conferring drought, water-deficit and/or high light tolerance to various plants can be obtained by using appropriate restriction sites using standard methods known to those of skill in the art. An active fragment refers to a continuous portion of the PGR5-encoding molecule (e.g., gene) that is less than the entire molecule. Such PGR5 gene fragments may encode the entire PGR5 protein or an active fragment and/or functional variant thereof.

In embodiments, non-essential nucleotides can be placed at the 5' and/or 3' end of the gene fragments (or the full-length PGR5 coding region) without affecting the functional properties of the fragment or molecule (e.g., in increasing water-deficit and/or high light tolerance, etc.). For example, the nucleotides encoding the PGR5 polypeptide may be conjugated to a nucleic acid encoding a signal or transit (or leader) sequence at the N-terminal end (for example) of the PGR5 polypeptide that co-translationally or post-translationally directs transfer of the PGR5 polypeptide. The nucleotide sequence may also be altered so that the encoded PGR5 polypeptide is conjugated to a linker, selectable marker, or other sequence for ease of synthesis, purification, and/or identification of the protein.

A transformed plant cell of the present disclosure can be produced by introducing into a plant cell a recombinant nucleic acid that encodes an exogenous PGR5 protein or active fragment thereof and expressing the PGR5 in the cell to increase tolerance of the plant to drought, water-deficit, high light, and/or other environmental or physical stresses that may induce the PGR5-dependent cyclic electron transport pathway, including, but not limited to, low temperatures, high salinity, and/or physical wounding of the plant.

Techniques for transforming a wide variety of plant cells are well known in the art and described in the technical and scientific literature. See, for example, Weising et al. (1988) Ann. Rev. Genet. 22:421-477. To express an exogenous PGR5 gene or fragment thereof in a plant cell, the gene can be combined with transcriptional and translational initiation regulatory sequences that direct the transcription of the gene and translation of the encoded protein in the plant cell.

For example, for over-expression, a constitutive plant promoter may be employed. A "constitutive" promoter is active under most environmental conditions and states of cell differentiation. Examples of constitutive promoters include the cauliflower mosaic virus (CaMV) 35S transcription initiation region, the 1'- or 2'-promoter derived from T-DNA of *Agrobacterium tumefaciens*, the ACT11 and Cat3 promoters from *Arabidopsis* (Huang et al. (1996) Plant Mol. Biol. 33:125-139 and Zhong et al. (1996) Mol. Gen. Genet. 251:196-203), the stearoyl-acyl carrier protein desaturase gene promoter from *Brassica napus* (Solocombe et al. (1994) Plant Physiol. 104: 1167-1176), and the GPc 1 and Gpc2 promoters from maize (Martinez et al. (1989) J. Mol. Biol. 208:551-565 and Manjunath et al. (1997) Plant Mol. Biol. 33:97-112).

Alternatively, a plant promoter may be employed to direct expression of the PGR5 nucleic acid in a specific cell type (e.g., tissue-specific promoters) or under more precise environmental or developmental control (e.g., inducible promoters). Examples of environmental conditions that may affect transcription by inducible promoters include anaerobic conditions, elevated temperature, the presence of light, contact with chemicals or hormones, or infection by a pathogen. Examples of such promoters include the root-specific ANR1 promoter (Zhang and Forde (1998) Science 279:407) and the photosynthetic organ-specific RBCS promoter (Khoudi et al. (1997) Gene 197:343).

For proper polypeptide expression, a polyadenylation region at the 3'-end of the coding region is preferably included. The polyadenylation region can be derived from the natural gene, from a variety of other plant genes, or from T-DNA.

A selectable marker can also be included in the recombinant nucleic acid to confer a selectable phenotype on plant cells. For example, the selectable marker may encode a protein that confers biocide resistance, antibiotic resistance (e.g., resistance to kanamycin, G418, bleomycin, hygromycin), or herbicide resistance (e.g., resistance to chlorosulfuron or Basta). Thus, the presence of the selectable phenotype indicates the successful transformation of the host cell. An exemplary selectable marker includes the beta-glucuronidase (GUS) reporter gene. In an exemplary embodiment, the GUS gene is operably linked a PGR5 promoter, and under the control of this promoter. The promoter may be the PGR5 promoter, or another promoter, such as a constitutive promoter or an inducible promoter, or any other appropriate promoter.

A recombinant nucleic acid that encodes exogenous PGR5 may be introduced into the genome of a desired plant host cell by a variety of conventional techniques. The recombinant nucleic acid including the exogenous PGR5 nucleic acid and one or more of the additional elements described above (e.g., promoter, selectable marker, etc.) may be incorporated into a plasmid for use in introducing the recombinant nucleic acid to the plant cell. Various plasmids and methods of use are known in the art and described in the literature.

Then, other techniques may be employed for introducing a plasmid or naked recombinant nucleic acid into the plant cell to be transformed. For example, the recombinant nucleic acid may be introduced directly into the genomic DNA of a plant cell using techniques such as, but not limited to, electroporation and microinjection of plant cell protoplasts, or the recombinant nucleic acid can be introduced directly to plant tissue using ballistic methods, such as DNA particle bombardment.

Microinjection techniques are known in the art and well described in the scientific and patent literature. The introduction of a recombinant nucleic acid using polyethylene glycol precipitation is described in Paszkowski et al. (1984) EMBO J. 3:2717-2722. Electroporation techniques are described in Fromm et al. (1985) Proc. Natl. Acad. Sci. USA 82:5824. Ballistic transformation techniques are described in Klein et al. (1987) Nature 327:70-73.

The recombinant nucleic acid may also be combined with suitable T-DNA flanking regions and introduced into a conventional *Agrobacterium tumefaciens* host vector, or other suitable vector. The virulence functions of the *Agrobacterium tumefaciens* host will direct the insertion of the recombinant nucleic acid including the PGR5 nucleic acid and adjacent marker into the plant cell DNA when the cell is infected by the bacteria. *Agrobacterium tumefaciens*-mediated transformation techniques, including disarming and use of binary vectors, are known to those of skill in the art and are well described in the scientific literature. See, for example, Horsch et al. (1984) Science 233:496-498; Fraley et al. (1983) Proc. Natl. Acad. Sci. USA 80:4803; and Gene Transfer to Plants, Potrykus, ed., Springer-Verlag, Berlin, 1995.

A further method for introduction of the recombinant nucleic acid into a plant cell is by transformation of plant cell protoplasts (stable or transient). Plant protoplasts are enclosed only by a plasma membrane and will therefore more readily take up macromolecules like exogenous DNA. These engineered protoplasts can be capable of regenerating whole plants. Suitable methods for introducing exogenous DNA into plant cell protoplasts include electroporation and polyethylene glycol (PEG) transformation. As used herein, "electroporation" is a transformation method in which a high concentration of plasmid DNA (containing exogenous DNA) is added to a suspension of host cell protoplasts, and the mixture shocked with an electrical field of about 200 to 600 V/cm. Following electroporation, transformed cells are identified by growth on appropriate medium containing a selective agent.

The presence and copy number of the exogenous PGR5 nucleic acid in a transgenic plant can be determined using methods well known in the art, e.g., Southern blotting analysis. Expression of the exogenous PGR5 nucleic acid in a transgenic plant may be confirmed by detecting the exogenous PGR5 mRNA or polypeptide in the transgenic plant. Methods for detecting and quantifying mRNA or proteins are well known in the art.

Transformed plant cells that are derived by any of the above transformation techniques, or other techniques now known or later developed, can be cultured to regenerate a whole plant. Such regeneration techniques rely on manipulation of certain phytohormones in a tissue culture growth medium, typically relying on a biocide or herbicide selectable marker that has been introduced together with the PGR5 nucleic acid. Plant regeneration from cultured protoplasts is described in Evans et al., Protoplasts Isolation and Culture, Handbook of Plant Cell Culture, pp. 124-176, MacMillilan Publishing Company, New York, 1983; and Binding, Regeneration of Plants, Plant Protoplasts, pp. 21-73, CRC Press, Boca Raton, 1985. Regeneration can also be obtained from plant callus, explants, organs, or parts thereof. Such regeneration techniques are described generally in Klee et al. (1987) Ann. Rev. Plant Phys. 38:467-486. Once the exogenous PGR5 nucleic acid has been confirmed to be stably incorporated in the genome of a transgenic plant, it can be introduced into other plants by sexual crossing. Any of a number of standard breeding techniques can be used, depending upon the species to be crossed.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

EXAMPLES

To investigate the function of PGR5-dependent CET throughout the *Arabidopsis thaliana* life cycle and in a distantly related plant, *A. thaliana* PGR5 (AtPGR5) was suppressed via RNA interference (RNAi), both AtPGR5 and loblolly pine (*Pinus taeda*) PGR5 (PtPGR5) were over-expressed in *A. thaliana*, and the expression patterns of these genes were examined. Compared to wild-type, the RNAi plants displayed decreased growth under high light when 2-3 weeks old, increased susceptibility to photodamage, and changes in several photosynthetic parameters. Constitutive over-expression of AtPGR5 or PtPGR5 caused increased tolerance of high light, drought, water-deficit and alterations in linear and cyclic electron transport. AtPGR5 promoter:GUS fusions and PtPGR5 tissue-specific northern blots indicated that PGR5 is predominantly expressed in young, rapidly expanding leaves and phloem. Wounding, exposure to excess light and low temperature all induced AtPGR5 transcription. In contrast to earlier reports, this example demonstrates that PGR5-dependent CET is important for the normal growth of young plants, even in the presence of NDH-dependent CET, and that it plays a significant, conserved role in protecting plants from the stromal redox imbalance that would otherwise be induced by stress.

Materials and Methods

Plant Materials and Growth Conditions

For experiments performed on artificial medium, *Arabidopsis thaliana* (Columbia ecotype) seeds were surface sterilized (McKinney et al., 2001) and germinated on MS medium (Gibco/BRL; adjusted to pH 5.7 with potassium hydroxide) containing 0.8% (wt/vol) Phytagar (Gibco/BRL), 1% sucrose, and 30 µg/ml kanamycin, except where indicated. Seedlings germinated on MS or on soil were grown under 150-200 µmol m-2 s-1 with a 16 hour photoperiod at 23° C., except where indicated.

PGR5 RNAi, Over-Expression, and Promoter-GUS Constructs

AtPGR5 RNAi construct: 200 bp from the AtPGR5 5' UTR and the 5' coding region (−100 to +100) were amplified from an *A. thaliana* leaf cDNA library (provided by E. McKinney and R. Meagher) and cloned in the sense orientation or the antisense orientation into pCRII-TOPO using the TOPO TA Cloning Kit (Invitrogen). One kb from the GUS coding sequence was amplified from pBI101 and also cloned into pCRII-TOPO. Using restriction enzyme sites in the vector, the antisense and sense sequences were then ligated sequentially on either side of the GUS coding sequence. The result was subcloned into pCAMBIA (CAMBIA) behind the cauliflower mosaic virus (CMV) 35S promoter.

AtPGR5 and PtPGR5 over-expression constructs (35S:AtPGR5 and 35S:PtPGR5): Full-length AtPGR5 cDNA was amplified from an *A. thaliana* leaf cDNA library (provided by E. McKinney and R. Meagher) with 5' UTR and 3' UTR primers. Using the sequence of DD55 (Warren and Covert, 2004) as the starting point, overlapping pieces of PtPGR5 were amplified from a *P. taeda* vascular cambium cDNA library (provided by J. Barnes and J. Dean) with vector- and gene-specific primers. After sequencing the resulting cDNA fragments, the full-length PtPGR5 cDNA was amplified with 5' UTR and 3' UTR primers. Using restriction sites designed into the PCR primers, full-length AtPGR5 and PtPGR5 cDNAs were subcloned as transcriptional fusions behind the CMV 35S constitutive promoter in pBIN19 (Bevan, (1984)).

AtPGR5 promoter: GUS construct: Genomic DNA was isolated from *A. thaliana* using the EZDNA Plant DNA Miniprep Kit (OmegaBio-tek). 1.1 kb from the AtPGR5 upstream region plus the first 30 bp of the coding region were amplified from *A. thaliana* genomic DNA. The product was cloned into pCRII-TOPO and subcloned via restriction sites in the PCR primers upstream of the GUS start codon in pBI101 (Clontech) to generate a translational fusion.

All transformation constructs, as well as corresponding empty control vectors, were transformed into *Esherichia coli* strain DH5α, sequenced, and transferred into *Agrobacterium tumefaciens* strain C58C1. *A. thaliana* plants were transformed by *Agrobacterium*-mediated vacuum infiltration (An et al., 1996; Bechtold and Pelletier, 1998). In all lines displaying the 3:1 Kan$^R$:Kan$^S$ ratio expected for a single insertion event, plants from the T3 or T4 generation were verified as transgenic by GUS staining, RNA blots, and/or immunoblots. The three RNAi and over-expression lines with the lowest and highest PGR5 expression levels, respectively, were selfed to produce T4 homozygous plants. Both T3 and T4 plants from these lines were used in the analysis of plant phenotypes. Plants containing empty vectors were indistinguishable transcriptionally and physically from wild-type plants (data not shown) so wild-type plants were used as non-treatment controls in many experiments.

Polyclonal Antibody Preparation

The AtPGR5 cDNA was subcloned into the pMALc2 vector (New England Biolabs) to generate the maltose-binding protein:PGR5 fusion protein construct, which was transformed into the RosettaBlue strain of *E. coli* (Novagen, Madison, Wis.) and induced with IPTG. After sonication and purification on an amylose resin column (New England Biolabs) the MBP:PGR5 fusion protein was concentrated with a YM-10 Centricon Centrifugal Filter (Millipore), and injected into rabbits to raise AtPGR5 antibodies. Western analysis of pre-immune and immune serum verified production of the AtPGR5 antibody in response to the fusion protein (data not shown).

Protein and RNA Blots

For protein immunoblots, *A. thaliana* total proteins were extracted in 2× running buffer (100 mM Tris, pH 6.8, 2% SDS, 5% b-mercaptoethanol, 15% glycerol, and bromophenol blue), boiled for five minutes, and centrifuged at 13,000 g for 10 minutes. The concentration of the supernatant was determined by the RC/DC Protein Concentration Kit (Biorad). Total plant proteins were run on a 15% SDS PAGE gel and stained with Coomassie blue. Equal loading of stained gels was verified by densitometry. Proteins were blotted onto nitrocellulose membranes and probed with the AtPGR5 antiserum or with a PORB antibody (provided by G. Armstrong and described by Franck et al., 2000) using the ECL Plus Western Blotting Detection System (Amersham Pharmacia Biotech).

*A. thaliana* and *P. taeda* total RNA was extracted as previously described (Chang, 1993; Weigal and Glazebrook, 2002; Warren and Covert, 2004), run on a denaturing gel, blotted onto nylon membranes and probed with either an AtPGR5- or PtPGR5-specific DNA probe according to a standard protocol (Ausubel et al., 1998). Northern analysis of *P. taeda* pollen was similar except the pollen was ground with glass beads before RNA extraction. Alterations in protein and transcript levels were measured with a phosphoimager and analyzed with ImageQuant software (Amersham Pharmacia Biotech).

Fluorescence Measurements

Chlorophyll fluorescence parameters were measured with a Diving PAM Underwater Fluorometer (Walz) by placing the fiber optic probe on the tops of attached leaves. $F_o$ (minimum fluorescence yield of open PSII centers) was determined at a light intensity of 5 μmol m-2 s-1. $F_m$ (maximum fluorescence yield of closed PSII centers in the dark) and $F_{m'}$ (maximum fluorescence yield of the closed PSII center under actinic light) were determined under saturating pulses (100 ms) of white light. $F_s$ (steady state fluorescence yield) was determined under actinic light intensities of 1-1000 μmol m-2 s-1. The efficiency of PSII photochemistry (φ) was calculated as $(F_m-F_o)/F_m$. NPQ was calculated as $(F_m-F_{m'})/F_{m'}$. $\phi_{PSII}$ was calculated as $(Fm'-Fs)/Fm'$. ETR was calculated as $\phi_{PSII} \times$ light intensity×0.5×0.85. qP was calculated as $(F_{m'}-F_s)/(F_{m'}-F_o)$. Replicated measurements (n=2-5) were taken on three different sets of plants with consistent results.

Detection of Reactive Oxygen Species

To measure $O_2$ production, plants were germinated and grown for two to three weeks on MS medium in sealed GA7 vessels (Magenta Corp.). As wounding also induces production of ROS, whole plants were gently removed from the medium, and immersed in a solution containing 0.025% NBT (Sigma), and 0.05% Tween 20 in potassium phosphate buffer, pH 7.0 (as described in Cuevas et al., 2004). The plants were vacuum infiltrated for five minutes, and illuminated until a dark blue formazan precipitate was visible in the leaves. The plants were bleached in 95% ethanol overnight to enhance visualization of the formazan precipitate.

Measurement of Anthocyanin Content

Mature leaves of three week old plants were collected and ground to powder in liquid nitrogen under low light. The powder was resuspended in 1% HCl in methanol on ice, and centrifuged at 10,000 g at 4° C. for five minutes. Anthocyanin content was calculated from spectroscopy measurements taken at 530 nm and 653 nm (calculated as described in Gould et al., 2000).

GUS Analyses

Young seedlings transformed with the AtPGR5:GUS construct were germinated on kanamycin selection medium, and when necessary, transferred to soil after two weeks. Plants were fixed and stained for GUS as described by An et al. (1996). To determine the AtPGR5 expression pattern in etiolated seedlings, seeds were sown on MS medium with 1% sucrose, wrapped in aluminum foil and placed in a light-sealed container at 22° C. in the dark for four days. The seedlings were then collected in a darkened room under a green safe light and placed directly in GUS staining solution (An et al., 1996). For wound analyses of AtPGR5:GUS expression, mature rosette leaves of five week old plants were gently crushed between the midvein and the leaf edge with padded forceps, then fixed and stained for GUS expression.

Stress Treatments

For tests of light tolerance, seeds were germinated directly on soil and grown at 150 µE/m²s for four weeks, then shifted to 2000 µmol m-2 s-1 for three weeks. For tests of drought tolerance, plants were grown under constant high light (2000 µmol m-2 s-1) in moist soil for three weeks. After three weeks, no more water was applied. To test the effect of light on gene expression, wild-type plants were grown for three weeks on soil at 150 µmol m-2 s-1, and shifted to 2000 ||mol m-2 s-1 for up to 12 hours. For cold treatments, seeds were sown on soil and grown for three weeks, then transferred to 4° for three days. Drought treatments for gene expression analysis were performed on wild-type plants according to a previous protocol (Yamaguchi-Shinozaki and Shinozaki, 1994). Briefly, seeds were sown on sterile SpectraMesh Nylon Filters (Spectrum) on MS medium containing 0 mM sucrose. After 10-14 days growth, the filters were removed and allowed to dry for up to three hours. For the sucrose treatments, seeds were sown on sterile SpectraMesh on MS medium containing 0 mM soluble carbohydrate, 100 mM sucrose, 100 mM glucose, or 100 mM mannitol. The seeds germinated and grew under constant light for five days. All plant materials were collected at the indicated intervals, plunged in liquid nitrogen, and stored at −80° C. until used in northern analyses. All treatments and RNA extractions were repeated at least twice.

Results

PGR5 is Important for Normal Growth Under High Light

Figure 2:
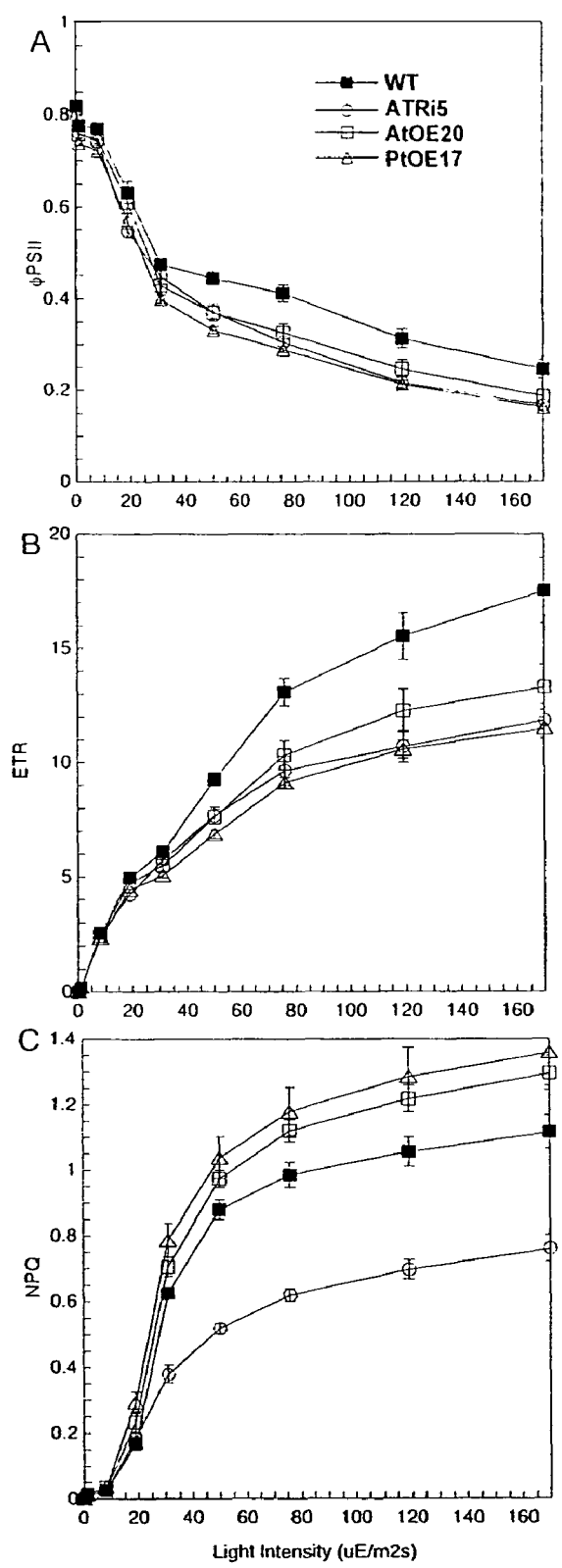
FIGS. 2A through 2C illustrate photosynthetic parameters in 4 week old *A. thaliana* wild-type (WT), RNAi (Ri5), and over-expression (AtOE20 and PtOE17) lines.

Using an RNA interference (RNAi) construct based upon portions of the AtPGR5 5'-untranslated region (UTR) and 5'-coding region, AtPGR5 expression was silenced in several independent lines. The two most suppressed lines, Ri5 and Ri9, contained only trace amounts of AtPGR5 transcript and protein (FIG. 1A and B), and they are described here in detail. Similar results were obtained with a third line that had a comparable level of AtPGR5 suppression (data not shown). Under moderate to high light (100-700 µmol m-2 s-1), the AtPGR5 RNAi plants displayed decreased PSII yield, decreased electron transport through PSII (ETR), and decreased NPQ when compared to wild-type (FIG. 2). These findings are consistent with the results from PGR5, a previously described point mutant in *A. thaliana* (Munekage et al., 2002; Munekage et al., 2004).

Figure 3:
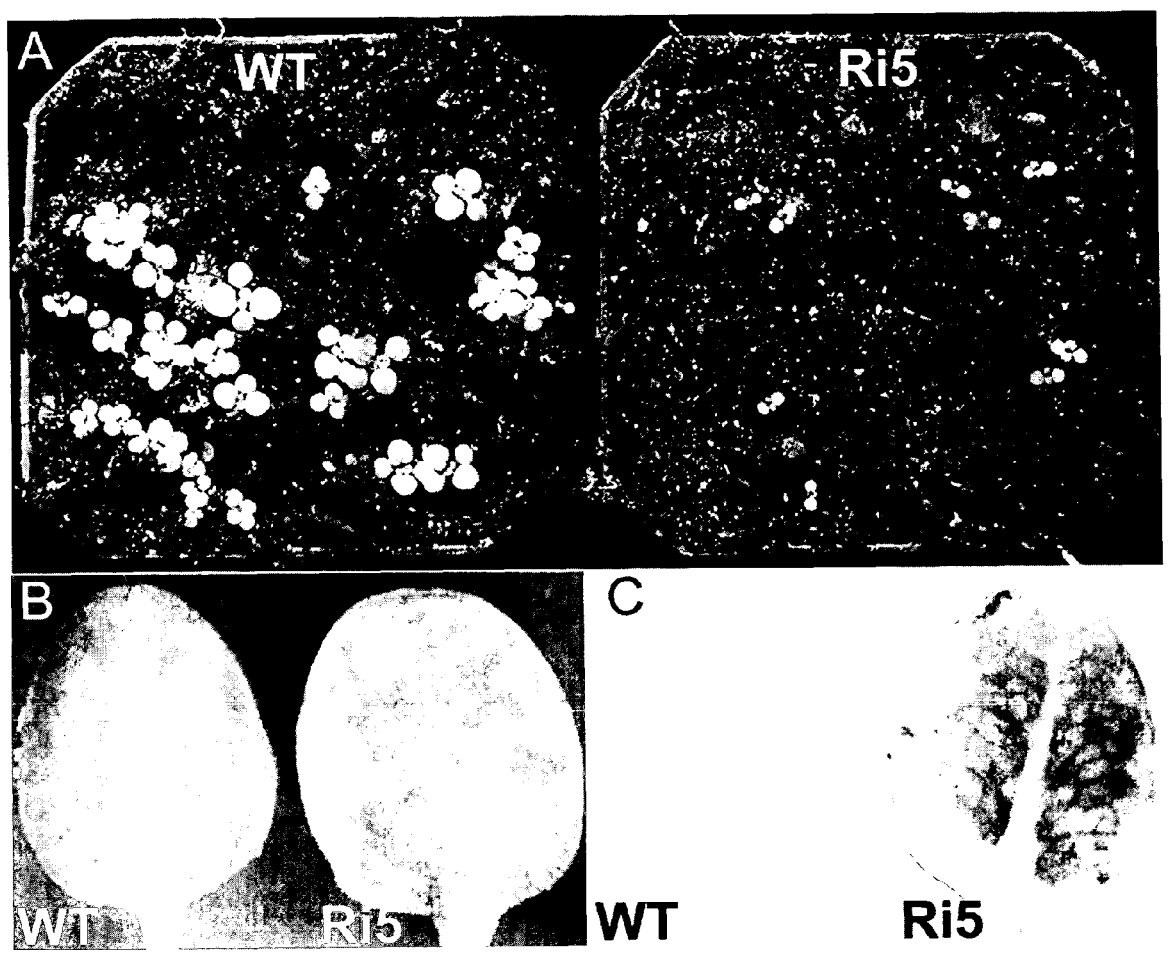
FIGS. 3A through 3C illustrate visible phenotypes of AtPGR5 RNAi lines.
Figure 4:
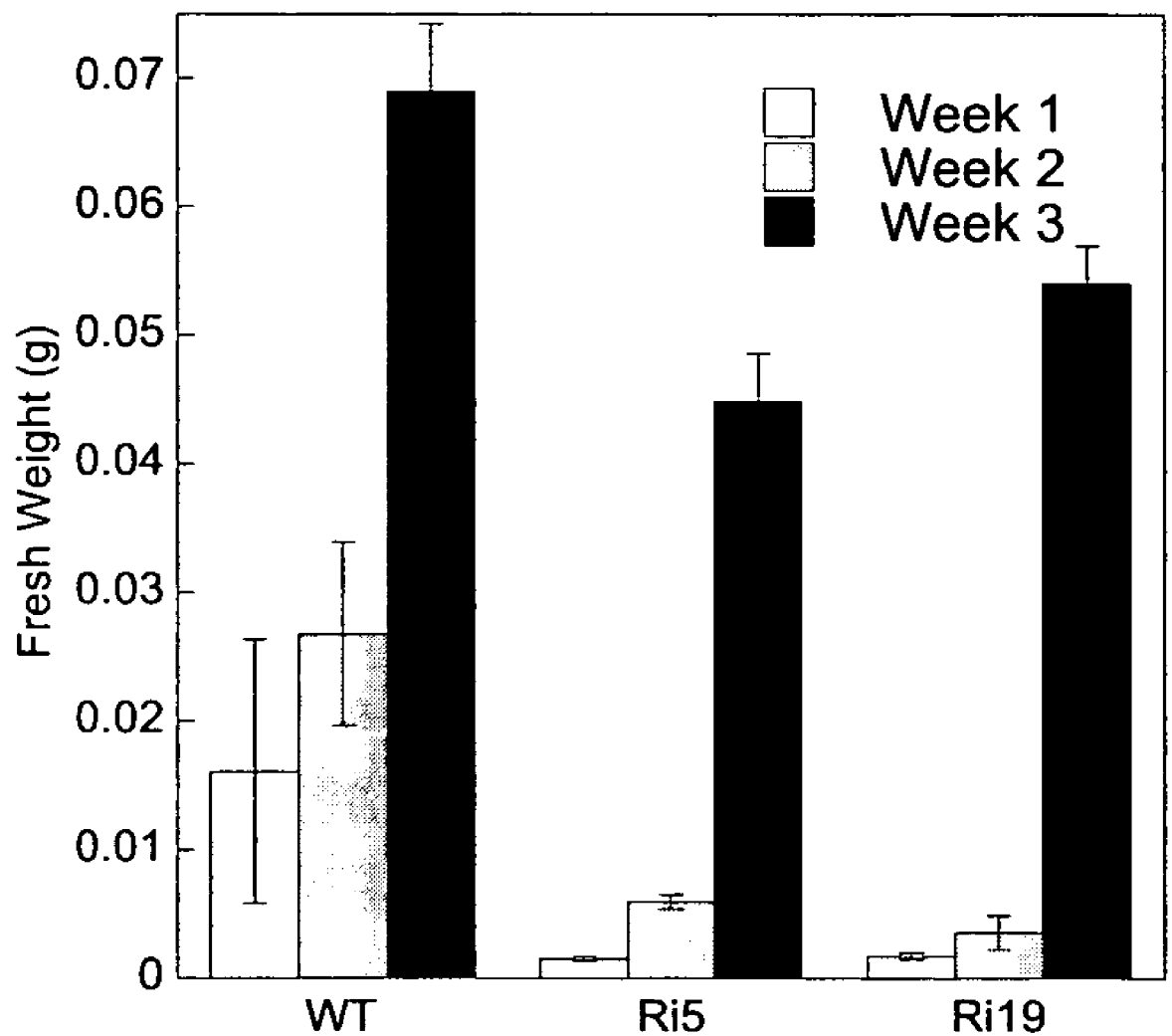
FIG. 4 is a bar graph of the average weight of rosettes from wild-type (WT) and AtPGR5 RNAi lines (Ri5 and Ri9) grown under high intensity light (2000 mE/m2s) on soil. Means±SE (n=5-10).

Because both types of AtPGR5 loss-of-function mutants exhibited decreased NPQ, it was hypothesized that the AtPGR5 RNAi lines would be reduced in their ability to tolerate bright light. Indeed, when these plants were germinated and grown on soil in a light intensity that approximates full sun (2000 µmol m-2 s-1), the fresh weight of their rosettes during the first two weeks was greatly reduced (e.g.,. only 13-22% of wild-type; FIG. 3A and FIG. 4). However, this defect did not persist; by the third week of growth, the weight of the AtPGR5 RNAi rosettes had started to catch up to that of wild-type (FIG. 4) and by the fourth to fifth week the two types of plants were approximately the same size (data not shown). RNAi suppression of AtPGR5 caused no changes in growth when the plants were grown under moderate (100-200 µmol m-2 s-1) or low light (50 µmol m-2 s-1; data not shown). Also, it did not affect growth when the plants were exposed to sudden increases in light intensity at three weeks of age (data not shown).

Suppression of PGR5 Causes Photodamage in a Sealed Environment

A lack of atmospheric $CO_2$ causes decreased Calvin Cycle activity and the over-reduction of the stromal redox carriers ferredoxin and $NADP^+$. This in turn leads to the formation of reactive oxygen species (ROS) that can damage the photosynthetic machinery and cause chlorosis. AtPGR5's apparent role in mediating NPQ, as illustrated in FIG. 2C, suggested that PGR5-dependent CET may act to protect plants from ROS-induced damage. Consistent with this idea, the leaves of AtPGR5 RNAi plants grown in airtight chambers for two weeks displayed chlorotic patches under moderate light (FIG. 3B). This chlorosis occurred whether plants were grown in media with or without 1% sucrose, but it diminished when the RNAi lines were shifted to open air, and did not appear if the plants were germinated and grown in an open environment (data not shown). To determine if the leaf chlorosis of the RNAi plants could be due to ROS accumulation, we applied nitro blue tetrazolium salt (NBT), which stains superoxide anion (Ottino and Duncan, 1997), to the leaves of RNAi and wild-type plants grown in airtight chambers. The AtPGR5 RNAi plants displayed a dramatic increase in ROS under these conditions as compared to wild-type (FIG. 3C).

Constitutive Over-Expression of AtPGR5 Causes Changes in Electron Transfer

Multiple, independent *A. thaliana* lines with increased AtPGR5 expression were created by transforming plants with a 35S promoter:AtPGR5 construct. The results presented below are derived from the most highly expressed line, AtOE20, which was representative of other lines expressing AtPGR5 at a high level. Line AtOE20 displayed dramatically increased AtPGR5 transcript levels and a two-fold increase in AtPGR5 protein (FIGS. 1C and 1D).

Chlorophyll fluorescence parameters were monitored to determine how over-expression of AtPGR5 affected LET and CET. AtPGR5 over-expression plants displayed decreased PSII photosynthetic yield (FIG. 2A), and a corresponding decrease in PSII ETR (FIG. 2B), as compared to wild-type plants. However, NPQ was elevated in over-expression lines in a light-dependent manner (FIG. 2C). This evidence suggests that although ectopically expressed PGR5 disrupts LET, it acts to increase NPQ by enhancing CET.

Constitutive Over-Expression of AtPGR5 Alters Stress Tolerance

Figure 5:
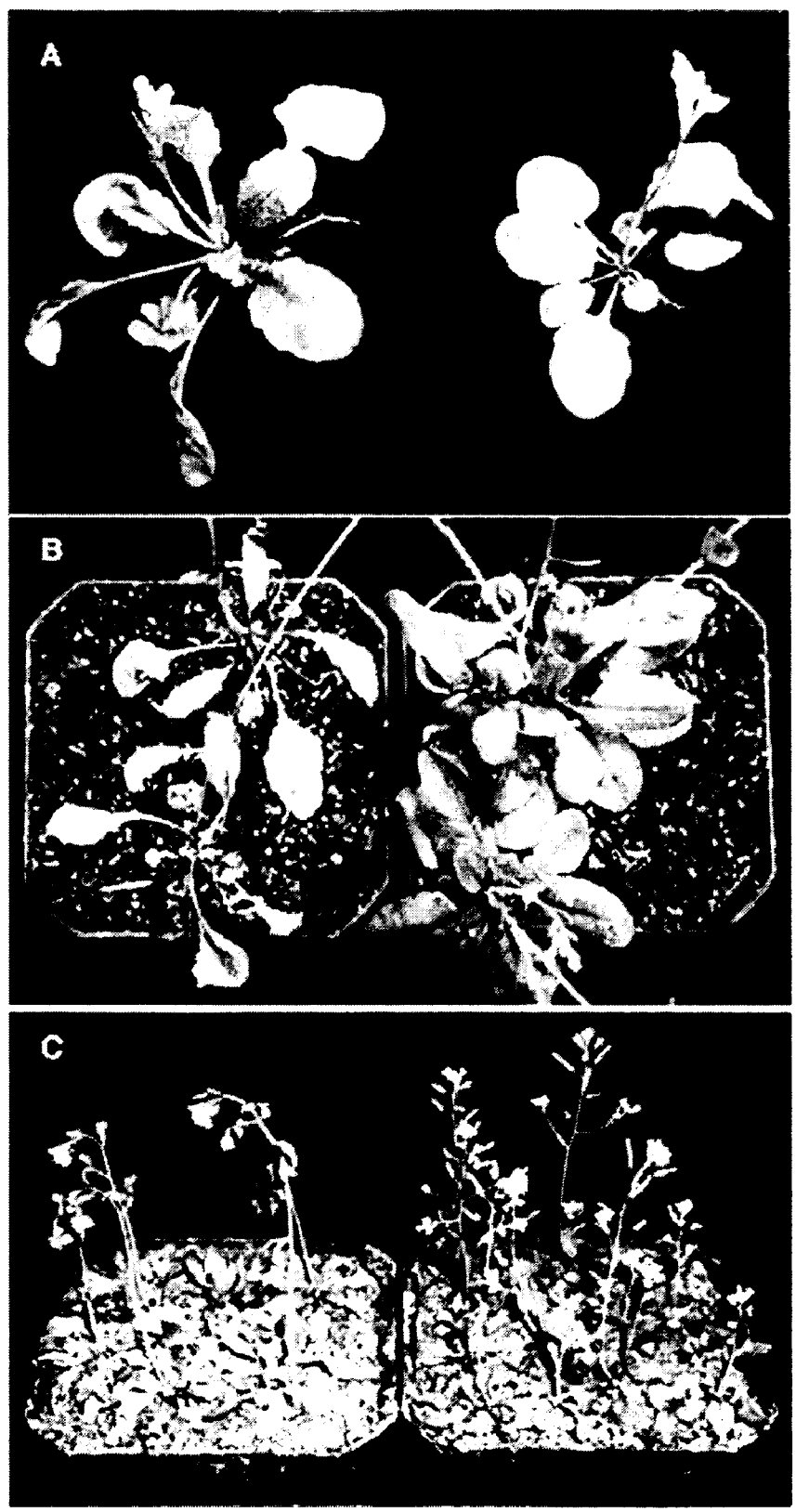
FIG. 5 illustrates the visible phenotypes of AtPGR5 and PtPGR5 over-expression (OE) lines in *A. thaliana*. In all panels, WT plants are on the left, OE plants are on the right, and the OE plants are representative of both 35S:AtPGR5 and 35S:PtPGR5 (engineered PGR5 gene from *Pinus taeda*) lines.

Because a reduction in AtPGR5 reduced high light tolerance, it was believed that over-expression of AtPGR5 would facilitate acclimation to high light. To investigate this possibility, 35S:AtPGR5 lines were grown in moderate light (200 µE/m²s) for four weeks, and then shifted to high light (2000 µE/m²s). Within four days, the anthocyanin level in the wild-type leaves had risen to 38±4 mg/g leaf tissue (mean±SD; n=4), and their appearance had changed dramatically (FIG. 5A, left). In contrast, the anthocyanin level in the 35S:AtPGR5 leaves only rose to 15±1 mg/g leaf tissue (mean±SD;

n=4) and the upper leaf surfaces remained bright green (FIG. 5A, right). As illustrated in FIG. 5B, three weeks after the shift to high light, the 35S:AtPGR5 plants were still growing and primarily green (FIG. 5B, right), while the wild-type plants grown under the same conditions were shriveled and dead (FIG. 5B, left). Wild-type plants maintained under moderate light for seven weeks remained healthy (data not shown), indicating that the sudden shift to high irradiance light accounted for the death of the wild-type plants.

When discarding old 35S:AtPGR5 plants, it was noticed that they often were very healthy-looking even if they had not been watered for some time. To test the possibility that they might be drought tolerant, 35S:AtPGR5 and wild-type plants were grown for three weeks and then watering was discontinued. After 3 weeks without water, the 35S:AtPGR5 plants remained green and upright (FIG. 5C, right) and the wild-type plants were brown and wilted (FIG. 5C, left). Wild-type plants grown under identical light conditions with plentiful water remained green and healthy (data not shown), therefore indicating that the wilting of the wild-type plants was due to a lack of water and not the concomitant high light treatment.

AtPGR5:GUS Expression is Developmentally Regulated

AtPGR5 is present in the chloroplasts of 4-5 week old wild-type plants grown in low intensity light, but little else is known about the regulation of AtPGR5 expression. In an effort to expand the understanding of AtPGR5's importance at different developmental stages, the AtPGR5 promoter-driven expression of the beta-glucuronidase (GUS) reporter gene was examined in five independent lines. Expression patterns common to all five lines are described in this example. AtPGR5:GUS was expressed in cotyledons during the seedling stage, as well as in all true leaves until at least two weeks after germination (FIG. 6A and 6B). By four weeks after germination AtPGR5:GUS expression was at its highest level in rapidly expanding and young, fully expanded rosette leaves, but it was only moderately expressed in emerging leaves and older leaves (FIG. 6C). In the emerging leaves, expression was initially concentrated at the apex and then it spread throughout the leaves as they expanded (FIG. 6C). By the fifth or sixth week after germination, AtPGR5:GUS expression had decreased significantly, with the remaining expression concentrated at the base of the oldest leaves and in the youngest leaves (FIG. 6D). After the seventh week there was little or no AtPGR5:GUS expression in any rosette leaves (data not shown).

AtPGR5:GUS was also expressed in inflorescence stems. Visual inspection of whole plants stained for GUS revealed that AtPGR5:GUS expression was highest at the top of the stem (data not shown). GUS staining of transverse sections from the top two inches of inflorescence stems from six week old plants revealed expression in primary cortical cells and phloem cells in the vascular bundles (FIG. 6E). After inducing secondary vascular tissue in the hypocotyls by continually decapitating the floral stem, AtPGR5:GUS was expressed primarily in the secondary phloem (FIG. 6F).

Analysis of the AtPGR5 regulatory region (−1100 to −1) with PLACE Signal Scan identified several putative regulatory motifs, such as etiolation-, pollen-, and endosperm-specific elements (FIG. 7), which suggests that AtPGR5 might be expressed in non-photosynthetic tissues. Consistent with this, AtPGR5:GUS was highly expressed in the cotyledons of dark-grown seedlings, as well as in mature stigmas, anthers, and pollen (FIGS. 6A and 6I). Although there was slight expression in the silique and ovary funicule, developing embryos did not express AtPGR5:GUS (data not shown). AtPGR5:GUS also was expressed in the hypocotyl and cotyledons as the embryos emerged from the seed coat, and in the aleurone cells associated with the seed coat (FIGS. 6G and 6H).

Immunoblots of total protein from adult plants verified that AtPGR5 is present in young emerging leaves, fully expanded leaves, older leaves, stems, and flowers, but not roots (data not shown).

Figure 8:
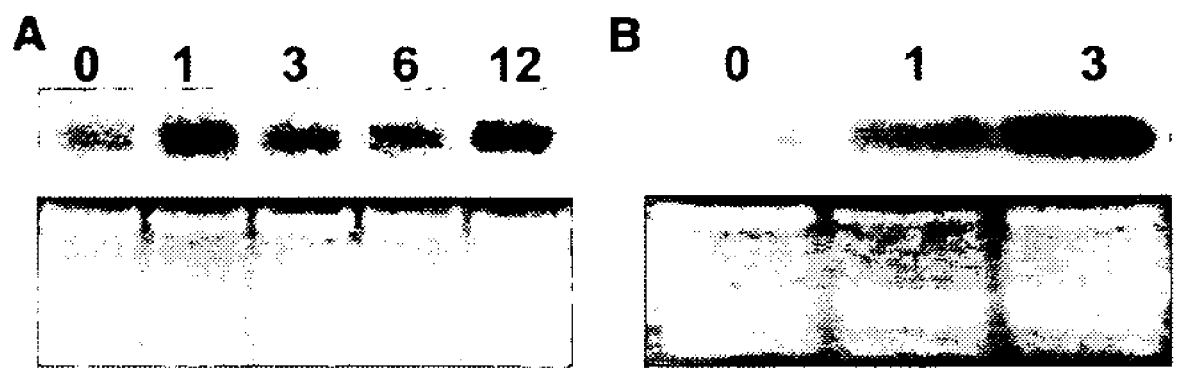
FIG. 8 illustrates northern hybridizations showing the effects of abiotic stress on AtPGR5 expression.

AtPGR5 is Up-Regulated by High Light and Other Stresses that Inhibit Calvin Cycle Activity Under normal $CO_2$ concentrations, photoinhibition can occur upon exposure to high light intensities. Based on AtPGR5's proposed role in photoprotection, and the presence of numerous putative light regulatory elements in the AtPGR5 promoter (FIG. 7), it was suspected that AtPGR5 might be induced by high irradiance. To test this theory, three week old wild-type plants were exposed to 2000 µE/m²s for up to 12 hours and northern analysis was used to visualize changes in AtPGR5 expression. After one hour of high light, AtPGR5 expression increased over 2-fold and it retained this approximate level for at least 12 hours (FIG. 8A).

Photoinhibition can also occur under moderate light if $CO_2$ assimilation is limited. Physiological stresses, such as wounding, cold, water-deficit/drought, and excess exogenous sucrose decrease $CO_2$ fixation and lead to elevated NPQ to prevent photoinhibition. Because of AtPGR5's apparent role in photoprotection, it seemed possible that transcription of AtPGR5 would rise in response to conditions that decrease $CO_2$ fixation. The fact that the AtPGR5 promoter has wound-, cold-, drought-, and sucrose-responsive elements further supported this theory (FIG. 7). Thus, wild-type plants were exposed to these four conditions and changes in gene expression were analyzed by GUS or northern analysis. GUS analysis of wounded leaves indicated that AtPGR5:GUS was up-regulated within an hour of wounding and that its expression was even higher 23 hours later (FIG. 6J). This up-regulation was not systemic; it was only seen at the wound site and in the surrounding veins. Northern analysis indicated that AtPGR5 was also up-regulated four-fold after three days of chilling at 4° C. (FIG. 8B). Dehydration caused about a 23% increase in AtPGR5 expression, and exogenous sucrose or glucose decreased AtPGR5 expression by about 24% (data not shown). Such effects were reproducible.

PGR5 Function Appears to be Conserved in a Distantly Related Plant Species

The PGR5 and NDH protein sequences are conserved throughout the plant kingdom. A notable exception to this rule, however, is the apparent absence of ndh genes in all *Pinus* species that have been examined to date. This finding suggests that this ancient and widely distributed genus has been an evolutionary success despite its probable lack of NDH-dependent CET. This raises the question of whether PGR5-dependent CET is likely to function in *Pinus*, and if the putative ortholog to AtPGR5 in loblolly pine (PtPGR5) could be its functional homolog. This possibility was supported by the high degree of sequence conservation between the two proteins encoded by these genes; outside of their chloroplast targeting sequences, PtPGR5 (SEQ ID NO: 5) and AtPGR5 (SEQ. ID. NO: 3) are about 76% identical to each other (data not shown).

Figure 6:
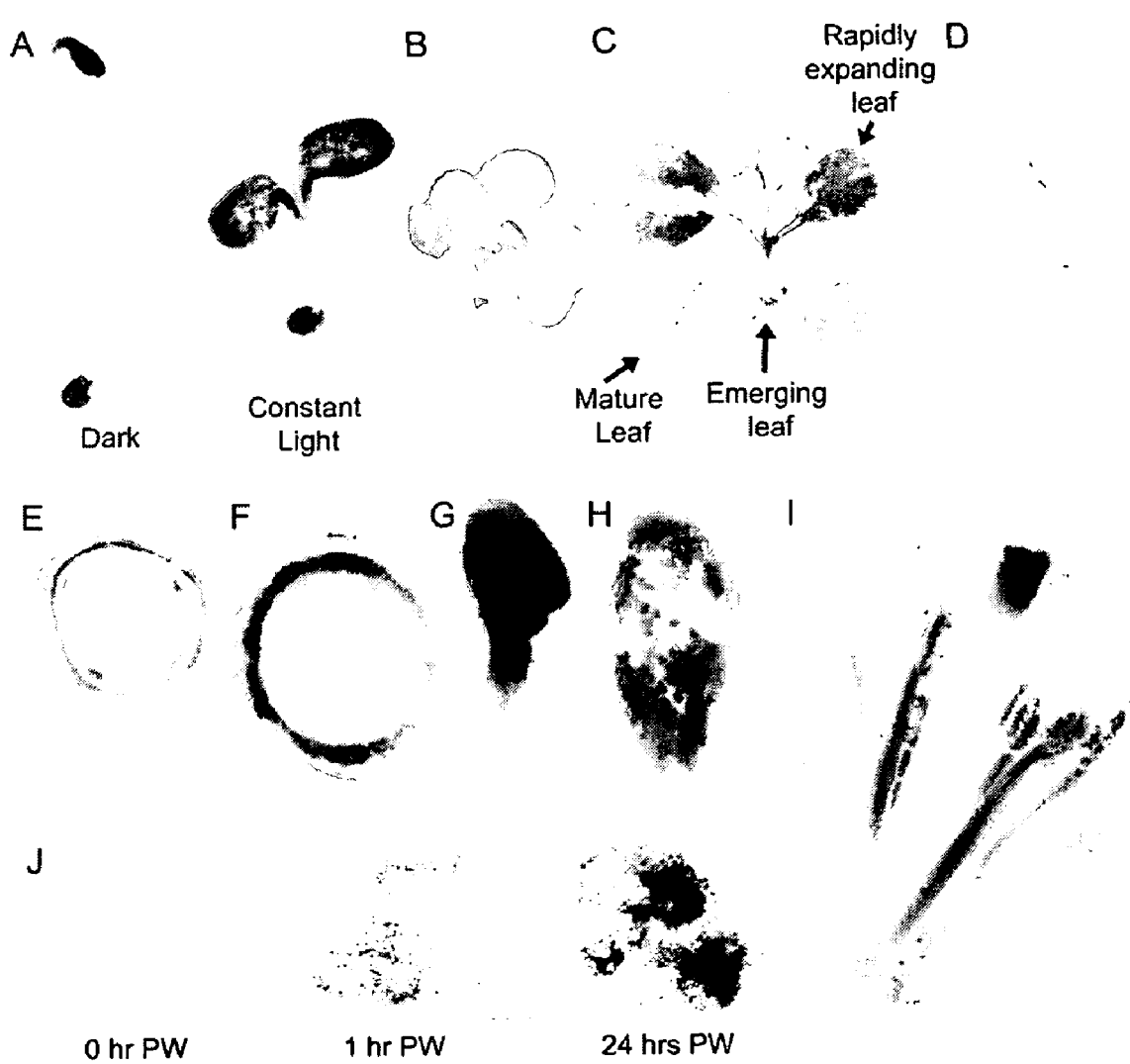
FIG. 6 illustrates AtPGR5:GUS expression patterns.
Figure 9:
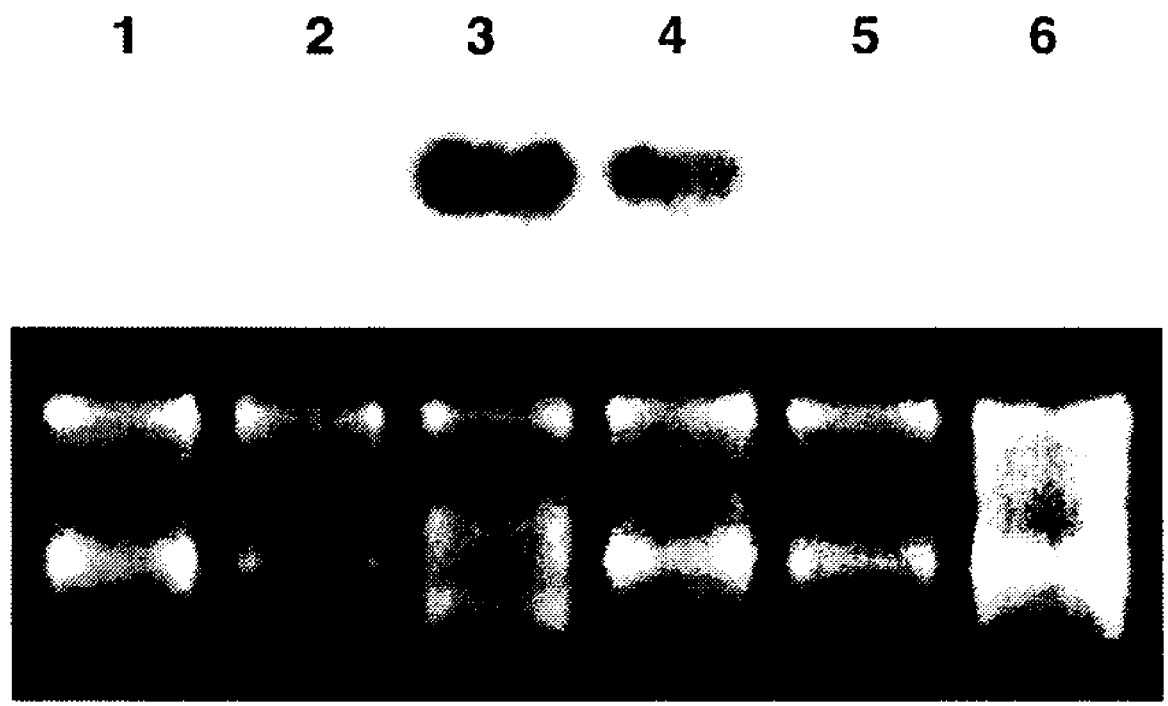
FIG. 9 illustrates northern analysis of PtPGR5 expression in different *P. taeda* tissues. RNA from various tissues was hybridized to PtPGR5 specific DNA probes. Lanes 1-6 correspond to RNA from shoot apical meristems (1), young succulent stems (2), mature needles (3), phloem (4), xylem (5), or roots (6). Corresponding RNA gel stained with ethidium bromide is shown in the lower panel.

Constitutive over-expression of PtPGR5 in *A. thaliana* (FIG. 1F) caused changes in electron transport, growth, and development similar to those seen in the AtPGR5 over-expression lines. When compared to wild type plants, 35S: PtPGR5 plants displayed an increased availability of PSI electron acceptors, increased plastoquinone reduction, decreased PSII quantum yield, and a corresponding decrease in PSII ETR (FIGS. 2A-2E). 35S:PtPGR5 lines also exhibited the same physical phenotypes as 35S:AtPGR5 plants: e.g., white cotyledons, and high tolerance of increased light intensity and drought (data not shown). Northern analysis of RNA from a variety of *P. taeda* tissues indicated that PtPGR5 was most strongly expressed in mature needles and phloem (FIG. 9), in a manner similar to that of AtPGR5 in *A. thaliana* (FIG. 6). PtPGR5 was also expressed at a relatively low level in the shoot apical meristem and in young stems (FIG. 9). Unlike AtPGR5, PtPGR5 expression was not detected in pollen (data not shown). However, upon examining the pollen from these two species, the *A. thaliana* pollen was mature while that from pine was not, because loblolly pine pollen does not reach maturity until it has been enclosed within a female cone for about one year. This offers a possible explanation for the observed differences in expression in pollen between the two species. The majority of the data, therefore, strongly suggests that PGR5 function is conserved between loblolly pine and *A. thaliana*. It is therefore believed that such function is likely to be conserved throughout the plant kingdom.

Discussion

PGR5 Mediates an Electron Transport Pathway Important for Normal Growth and Photoprotection Plants with decreased amounts of AtPGR5 due to RNAi suppression exhibited decreased PSI electron acceptors, PSII yield, PSII ETR, and NPQ, as well as increased PQ reduction (FIG. 2). In contrast to previous conclusions that loss of PGR5 function causes no discernable phenotype in intact plants (Munekage et al., 2002; Munekage et al., 2004), the present examples demonstrate that AtPGR5 RNAi seedlings exposed to high light grew more slowly than wild-type seedlings. This novel phenotype is the first evidence that PGR5-dependent CET is so important for normal growth in young plants, even in the presence of NDH-dependent CET. Furthermore, the high light condition (2000 $\mu E/m^2 s$) at which this phenotype was observed approximates the intensity of full sunlight and, therefore, represents a condition to which *A. thaliana* plants and other plant species are likely to be exposed in nature.

One explanation for the reduced growth of the AtPGR5 RNAi lines in high light is that PGR5-dependent CET is an important source of ATP in such an environment. Previous studies have indicated that plants acclimated to high light (600-2000 $\mu E/m^2 s$) have increased amounts of Calvin Cycle, PSII, and $Cb_6/f$ complex proteins, as well as increased ATP synthase (Walker, 2005). Synthesis of these and other proteins requires ATP, and this may account in part for the elevated ATP synthase activity observed in plants grown under high light. In addition, plants acclimated to high light exhibit elevated $CO_2$ fixation, and thus require more ATP for this process than plants grown under low or moderate light. Finally, decreased $CO_2$ fixation in the presence of the PGR5-dependent CET inhibitor antimycin A indicates that CET is an important energy source for $CO_2$ fixation under high light. These data all support the idea that plants require more ATP for proper growth when acclimated to high light than they do in lower light environments, and that the AtPGR5 RNAi lines grew more slowly than wild-type because PGR5-dependent CET is an important source of ATP under high light in young plants.

The decreased growth of the AtPGR5 RNAi plants in high light could also be a photoprotective mechanism. Plants acclimated to high light produce thick leaves with a small surface area (Walters and Horton, 1994; Pearcy, 1998; Bailey et al., 2004; Muller-Moule et al., 2004). These characteristics enable plants to minimize light exposure. It is possible, therefore, that because PGR5-dependent CET mediates NPQ and stromal redox balance, the AtPGR5 RNAi plants grew more slowly than wild-type to minimize absorption of excess light, thereby preventing photoinhibition.

Decreased AtPGR5 led to visible photodamage and to the accumulation of ROS when AtPGR5 RNAi plants were grown in an airtight environment under moderate light. Under these conditions, the atmospheric $CO_2$ concentration decreases over time and the Calvin Cycle is inhibited. In the absence of AtPGR5, this apparently led to over-reduction of the LET pathway and stromal redox carriers, and subsequently to the formation of ROS. The present data suggests, therefore, that PGR5-dependent CET prevents over-reduction of the stroma when the Calvin Cycle is suppressed by sequestering electrons from NADPH and reduced Fd and inducing NPQ. These results also imply that PGR5-dependent CET provides an alternative electron transport pathway for excess light energy that can not be compensated for by NDH-dependent CET. The biochemical differences between PGR5, ndh and crr mutants (crr mutants affect ndhB subunit synthesis) support this theory (Munekage et al., 2004). While disruption of NDH activity causes no change in LET or CET under normal growth conditions, reduced PGR5 activity causes alterations in CET, LET, and decreased NPQ. It is likely, therefore, that PGR5-dependent CET prevents stroma over-reduction, and subsequent photoinhibition, independent of NDH-dependent CET.

The timing of the AtPGR5 RNAi phenotypes suggests that PGR5-dependent CET is most important when plants are young. Furthermore, AtPGR5:GUS expression was highest in seedlings, and in young, expanding leaves. Consistent with these results, photosynthetic mechanisms decline early in *A. thaliana*, even before the leaves fully expand. The resulting decline in $CO_2$ assimilation along with a high chlorophyll content causes an imbalance between energy intake and utilization, which can lead to photodamage and photoinhibition. To prevent photoinhibition, NPQ gradually increases during the life of the plants, and peaks during the beginning of senescence. This process correlates with the expression patterns of AtPGR5:GUS and PtPGR5, and with the AtPGR5 RNAi phenotypes in young plants. Therefore, PGR5-dependent CET may be particularly important in younger leaf tissues because there is a significant need for photoprotection. The fact that three-week-old AtPGR5 RNAi plants still resembled WT plants when shifted from moderate to high light also adds emphasis to the idea that the importance of AtPGR5 function may diminish as plants approach maturity.

Elevated PGR5 Supports the Role of PGR5-Dependent CET in Photoprotection

Constitutive over-expression of PGR5 caused a domino effect in which there was an increase in electrons moving from PSI to Fd to PQ. It is believed that this increased CET activity led to an increase in $\Delta pH$, which in turn elevated NPQ. Because PGR5-dependent CET is more prominent upon over-expression, PGR5 appears to be a rate-limiting component of this alternative photosynthetic pathway. Although its lack of a metal binding motif makes it unlikely that PGR5 is itself an electron carrier, it may recruit components or stabilize a CET complex. CET has been proposed to occur in a complex that is physically separated from the LET machinery during the transition from dark to light (Joliot and Joliot, 2002), so it is possible that PGR5 localizes to specific regions of the thylakoid membranes.

After a sudden shift in light intensity, the prevention of stromal over-reduction and increased NPQ in the PGR5 over-expression lines apparently suppressed the formation of anthocyanin, a pigment that protects mesophyll cells by absorbing excess light. In addition, after the sudden increase in irradiance, these photoprotective mechanisms seem to have extended the survival of plants with elevated PGR5.

PGR5 over-expression plants also consistently out-lasted wild-type plants of the same size under drought conditions. Given PGR5's role in photoprotection under $CO_2$ limiting conditions, this result is in accordance with the idea that drought-induced plant death is not simply a function of cellular dehydration, but is in fact accelerated by stromal overreduction and the consequent damage caused by ROS (Dat et al., 2000). Regardless of the under-lying mechanisms, both the drought and high light tolerance phenotypes of the PGR5 over-expression plants support the potential agricultural utility of PGR5 recombinant plant varieties.

Specific Developmental Processes and Abiotic Stressors Regulate AtPGR5 Expression In addition to its expression in cotyledons and young leaves, AtPGR5:GUS was expressed in phloem, certain reproductive tissues, aleurone cells, and etiolated seedlings. For example, AtPGR5 expression in the phloem is likely due to the presence of chloroplasts in sieve companion cells, and stigmata, filaments, and anthers contain a variety of plastids, some of which are photosynthetically active. In contrast, etiolated seedlings, mature pollen, and aleurone cells are not photosynthetically active, but etiolated seedlings and pollen do contain plastids that either are poised to become, or previously were, chloroplasts. Therefore, the presence of photosynthetic proteins in these tissues is not entirely unlikely. However, it is unclear why the AtPGR5 promoter is activated in aleurone cells, which contain only starch-bearing plastids.

Abiotic stress can lead to photoinhibition by causing an imbalance in energy acquisition and utilization. The consequent alterations in chloroplast redox status regulate the expression of both chloroplast- and nuclear-encoded genes whose products are involved in photoprotection or other processes. AtPGR5's expression was induced by elevated light, wounding, and chilling, thus indicating that alterations in the chloroplast redox status activate the transcription of AtPGR5 to increase PGR5-dependent CET and prevent photodamage.

PGR5-Dependent CET May Compensate for NDH Deficiency in Pinus Species

Two studies have raised questions about the presence of NDH-dependent CET in Pinus species. In the first of these, the chloroplast genome of black pine (Pinus thunbergii) was found to lack functional copies of the eleven genes encoding NDH subunits (Wakasugi et al., 1994). In the second study, ndhF was successfully amplified from all of the nonflowering vascular plant divisions, including conifers, but it could not be amplified from any of the three pine species (including loblolly pine) that were tested (Neyland and Urbatsch, 1996). Assuming that NDH is not present in Pinus, and based on the results of the present examples, it is believed that PGR5-dependent CET alone provides sufficient photoprotection and modulation of the stromal redox state in this genus.

Based upon the phenotypes of PGR5 RNAi and over-expression lines and the analysis of PGR5 expression in wild-type plants, it is believed that PGR5-dependent CET is important not only for normal growth in young Arabidopsis plants, but also to maintain the proper redox status when these plants are exposed to stress conditions. Although it appears that NDH-dependent CET can compensate for PGR5-dependent CET in maintaining the ATP:NADPH ratio for the Calvin Cycle under low light, the present data indicate that NDH cannot compensate for PGR5 in sunlight or stress conditions in young plants.

REFERENCES

All of the references are incorporated herein by reference.

An, Y.-Q., Huang, S., McDowell, J. M., McKinney, E. C., and Meagher, R. B. (1996). Conserved expression of the *Arabidopsis* ACT1 and ACT3 actin subclass in organ primordia and mature pollen. Plant Cell 8, 15-30.

Ausubel, F. M., Brent, R., Kingston, R. E., Moore, D. D., Seidman, J. G., Smith, J. A., and Struhl, K. (1998). Current protocols in molecular biology. (New York, N.Y.: John Wiley and Sons Inc.).

Bechtold, N., and Pelletier, G. (1998). In planta *Agrobacterium*-mediated transformation of adult *Arabidopsis thaliana* plants by vacuum infiltration. Methods Mol. Biol. 82, 259-266.

Bevan, M. (1984). Binary *Agrobacterium* vectors for plant transformation. Nucl. Acids Res. 12, 8711-8721.

Chang, S., Puryear, J., Cairney, J. (1993). A simple and effective method for isolating RNA from pine trees. Plant Molec. Biol. 11, 113-116.

Cuevas, J. C., Diego, S. H., Marina, M., and Ruiz, O. (2004). Do polyamines modulate the *Lotus glaber* NADPH oxidation activity induced by the herbicide methyl viologen? Func. Plant Biol. 31, 921-928.

Franck, F., Sperling, U., Frick, G., Pochert, B., van Cleve, B., Apel, K., and Armstrong, G. A. (2000). Regulation of etioplast pigment-protein complexes, inner membrane architecture, and protochlorophyllide a chemical heterogeneity by light-dependent NADPH:protochlorophyllide oxidoreductases A and B. Plant Physiol 124, 1678-1696.

Gould, K. S., Markham, K. R., Smith, R. H., and Goris, J. J. (2000). Functional role of anthocyanins in the leaves of *Quintinia serrata* A. Cunn. J. Exp. Bot. 51, 1107-1115.

Higo, K., Ugawa, Y., Iwamoto, M., and Korenaga, T. (1999). Plant cis-acting regulatory DNA elements (PLACE) database: 1999. Nucl. Acids Res. 27, 297-300.

Joliot, P., and Joliot, A. (2002). Cyclic electron transfer in plant leaf. Proc Natl Acad Sci USA 99, 10209-10214.

Munekage, Y., Hojo, M., Meurer, J., Endo, T., Tasaka, M., and Shikanai, T. (2002). PGR5 is involved in cyclic electron flow around photosystem I and is essential for photoprotection in *Arabidopsis*. Cell 110, 361-371.

Munekage, Y., Hashimoto, M., Miyake, C., Tomizawa, K., Endo, T., Tasaka, M., and Shikanai, T. (2004). Cyclic electron flow around photosystem I is essential for photosynthesis. Nature 429, 579-582.

Neyland, R., and Urbatsch, L. E. (1996). The ndhf chloroplast gene detected in all vasular plant divisions. Planta 200, 273-277.

Schreiber, U., Klughammer, C., and Neubauer, C. (1988). Measuring P700 absorbance changes around 830 nm with a new type of pulse modulation system. Z. Naturforsch. 43C, 686-698.

Wakasugi, T., Tsudzuki, J., Ito, S., Nakashima, K., Tsudzuki, T., and Sugiura, M. (1994). Loss of all ndh genes as determined by sequencing the entire chloroplast genome of the black pine *Pinus thunbergii*. Proc. Natl. Acad. Sci. USA 91, 9794-9798.

Walker, R. G. (2005). Towards an understanding of photosynthetic acclimation. J. Exp. Bot. 56, 435-447.

Warren, J. A., and Covert, S. F. (2004). Differential expression of pine and *Cronartium quercuum* f. sp *fusiforme* genes in fusiform rust galls. Appl. Environ. Microbiol. 70, 441-451.

Weigal, B., and Glazebrook, J. (2002). *Arabidopsis*, a laboratory manual. (Cold Spring Harbor: Cold Spring Harbor Press).

Yamaguchi-Shinozaki, K., and Shinozaki, K. (1994). A novel cis-acting element in an *Arabidopsis* gene is involved in responsiveness to drought, low-temperature, or high-salt stress. Plant Cell 6, 251-264.

What is claimed is:

1. A transformed plant cell comprising: an exogenous nucleic acid that encodes a proton gradient regulation 5 (PGR5) polypeptide, wherein the PGR5 polypeptide increases tolerance of the transformed plant cell, or a plant grown therefrom, relative to a corresponding wild-type plant cell or plant, to one or more conditions selected from: high light, water-deficit, and drought.

2. The transformed plant cell of claim 1, wherein the PGR5 polypeptide is selected from:
   an *Arabidopsis thaliana* PGR5 (AtPRG5) polypeptide having the amino acid sequence of SEQ ID NO: 3; functional variants of AtPRG5 and homologs of AtPRG5 having an amino acid sequence with at least 59% sequence identity to SEQ ID NO: 3; a *Pinus taeda* PGR5 (PtPGR5) polypeptide having the amino acid sequence of SEQ ID NO: 5; and functional variants of PtPRG5 and homologs of PtPRG5 having an amino acid sequence with at least 59% sequence identity to SEQ ID NO: 5.

3. The transformed plant cell of claim 2, wherein the exogenous nucleic acid encodes for a PGR5 polypeptide selected from: the *Arabidopsis thaliana* PGR5 (AtPRG5) polypeptide having the amino acid sequence of SEQ ID NO: 3 and the *Pinus taeda* PGR5 (PtPGR5) polypeptide having the amino acid sequence of SEQ ID NO: 5.

4. The transformed plant cell of claim 1, further comprising a nucleic acid encoding a promoter, wherein the promoter controls expression of the exogenous nucleic acid.

5. The transformed plant cell of claim 4, wherein the promoter directs over-expression of the exogenous nucleic acid relative to expression of a PGR5 nucleic acid in a corresponding wild-type cell.

6. The transformed plant cell of claim 4, wherein the promoter is selected from: a stress-inducible promoter, a tissue-specific promoter, and a constitutive promoter.

7. The transformed plant cell of claim 4, wherein the promoter is a cauliflower mosaic virus 35S promoter.

8. The transformed plant cell of claim 1, further comprising a nucleic acid encoding a selectable marker.

9. The transformed plant cell of claim 1, wherein the plant cell is a dicot plant cell.

10. The transformed plant cell of claim 1, wherein the plant cell is an *Arabidopsis thaliana* cell.

11. The transformed plant cell of claim 1, wherein the plant cell is naturally light-sensitive.

12. The transformed plant cell of claim 1, wherein the plant cell is naturally drought-sensitive.

13. A transgenic plant grown from the plant cell of claim 1.

14. A transformed plant cell comprising: an exogenous nucleic acid that encodes a proton gradient regulation 5 (PGR5) polypeptide, wherein the PGR5 polypeptide increases the activity of PGR5-dependent cyclic electron transport in the transformed plant cell or a plant grown therefrom relative to a corresponding wild-type plant cell or plant.

15. The transformed plant cell of claim 14, wherein the PGR5 polypeptide is selected from: an *Arabidopsis thaliana* PGR5 (AtPRG5) polypeptide having the amino acid sequence of SEQ ID NO: 3; functional variants of AtPRG5 and homologs of AtPRG5 having an amino acid sequence with at least 59% sequence identity to SEQ ID NO: 3; a *Pinus taeda* PGR5 (PtPGR5) polypeptide having the amino acid sequence of SEQ ID NO: 5; and
   functional variants of PtPRG5 and homologs of PtPRG5 having an amino acid sequence with at least 59% sequence identity to SEQ ID NO: 5.

16. A transformed plant cell comprising a recombinant nucleic acid comprising:
   an exogenous nucleic acid that encodes a proton gradient regulation 5 (PGR5) polypeptide, and
   a nucleic acid encoding a promoter, wherein the promoter induces over-expression of the recombinant nucleic-acid relative to the expression of a PGR5 nucleic acid in a corresponding wild-type plant cell, and wherein the over-expression of the recombinant nucleic acid increases tolerance of the transformed plant cell, or a plant grown therefrom, to one or more conditions selected from: high light, water-deficit, and drought.

17. The transformed plant cell of claim 16,
   wherein the PGR5 polypeptide is selected from: an *Arabidopsis thaliana* PGR5 (AtPRG5) polypeptide having the amino acid sequence of SEQ ID NO: 3; functional variants of AtPRG5 and homologs of AtPRG5 having an amino acid sequence with at least 59% sequence identity to SEQ ID NO: 3; a *Pinus taeda* PGR5 (PtPGR5) polypeptide having the amino acid sequence of SEQ ID NO: 5; and functional variants of PtPRG5 and homologs of PtPRG5 having an amino acid sequence with at least 59% sequence identity to SEQ ID NO: 5.

18. A transgenic plant comprising: an exogenous nucleic acid that encodes a proton gradient regulation 5 (PGR5) polypeptide, wherein the PGR5 polypeptide increases tolerance of the transformed plant, relative to a corresponding wild-type plant, to conditions selected from: high light, water-deficit, and drought.

19. The transgenic plant of claim 18, wherein the PGR5 polypeptide is selected from: an *Arabidopsis thaliana* PGR5 (AtPRG5) polypeptide having the amino acid sequence of SEQ ID NO: 3; functional variants of AtPRG5 and homologs of AtPRG5 having an amino acid sequence with at least 59% sequence identity to SEQ ID NO: 3; a *Pinus taeda* PGR5 (PtPGR5) polypeptide having an the amino acid sequence of SEQ ID NO: 5; and
   functional variants of PtPRG5 and homologs of PtPRG5 having an amino acid sequence with at least 59% sequence identity to SEQ ID NO: 5.

20. The transgenic plant of claim 19, wherein the exogenous nucleic acid encodes for a polypeptide selected from: the *Arabidopsis thaliana* PGR5 (AtPRG5) polypeptide having the amino acid sequence of SEQ ID NO: 3 and the *Pinus taeda* PGR5 (PtPGR5) polypeptide having the amino acid sequence of SEQ ID NO: 5.

21. The transgenic plant of claim 18, further comprising a nucleic acid encoding a promoter, wherein the promoter controls expression of the PGR5 polypeptide.

22. The transgenic plant of claim 21, wherein the promoter induces higher levels of expression of PGR5 in the transformed plant than in an equivalent wild-type plant that does not comprise the exogenous nucleic acid encoding for PGR5 or the promoter.

23. The transgenic plant of claim 21, wherein the promoter is selected from: a stress-inducible promoter, a tissue-specific promoter, and a constitutive promoter.

24. The transgenic plant of claim 21, wherein the promoter is a cauliflower mosaic virus 35S promoter.

25. The transgenic plant of claim 18, further comprising a nucleic acid encoding a selectable marker.

26. The transgenic plant of claim 18, wherein the plant is a dicot.

27. The transgenic plant of claim 18, wherein the plant is *Arabidopsis thaliana*.

28. The transgenic plant of claim 18, wherein the plant is naturally light-sensitive.

29. The transgenic plant of claim 18, wherein the plant is naturally drought-sensitive.

30. A transgenic plant comprising: an exogenous nucleic acid that encodes a proton gradient regulation 5 (PGR5) polypeptide, wherein the expression of PGR5 increases the activity of PGR5 dependent cyclic electron transport in the transgenic plant relative to a corresponding wild-type plant.

31. The transgenic plant of claim 30, wherein the PGR5 polypeptide is selected from: an *Arabidopsis thaliana* PGR5 (AtPRG5) polypeptide having the amino acid sequence of SEQ ID NO: 3; functional variants of AtPRG5 and homologs of AtPRG5 having an amino acid sequence with at least 59% sequence identity to SEQ ID NO: 3; a *Pinus taeda* PGR5 (PtPGR5) polypeptide having the amino acid sequence of SEQ ID NO: 5; and functional variants of PtPRG5 and homologs of PtPRG5 having an amino acid sequence with at least 59% sequence identity to SEQ ID NO: 5.

32. A transformed plant comprising a recombinant nucleic acid comprising:
an exogenous nucleic acid that encodes a proton gradient regulation 5 (PGR5) polypeptide and
a nucleic acid encoding a promoter, wherein the promoter induces over-expression of PGR5 relative to a corresponding wild-type plant and wherein the over-expression of PGR5 increases tolerance of the transformed plant cell, or a plant grown therefrom, to one or more conditions selected from: high light, water-deficit, and drought.

33. The A transformed plant of claim 32,
wherein the PGR5 polypeptide is selected from: an *Arabidopsis thaliana* PGR5 (AtPRG5) polypeptide having the amino acid sequence of SEQ ID NO: 3; functional variants of AtPRG5 and homologs of AtPRG5 having an amino acid sequence with at least 59% sequence identity to SEQ ID NO: 3; a *Pinus taeda* PGR5 (PtPGR5) polypeptide having the amino acid sequence of SEQ ID NO: 5; and functional variants of PtPRG5 and homologs of PtPRG5 having an amino acid sequence with at least 59% sequence identity to SEQ ID NO: 5.

34. A method of producing a transformed plant cell comprising:
introducing into a plant cell an exogenous nucleic acid that encodes a proton gradient regulation 5 (PGR5) polypeptide, and
expressing the PGR5 polypeptide in the cell, wherein the transformed plant cell has increased tolerance, relative to a corresponding wild-type plant cell, to one or more conditions selected from: high light, water-deficit, and drought.

35. The method of producing a transformed plant cell of claim 34,
wherein the PGR5 polypeptide is selected from: an *Arabidopsis thaliana* PGR5 (AtPRG5) polypeptide having the amino acid sequence of SEQ ID NO: 3; functional variants of AtPRG5 and homologs of AtPRG5 having an amino acid sequence with at least 59% sequence identity to SEQ ID NO: 3; a *Pinus taeda* PGR5 (PtPGR5) polypeptide having the amino acid sequence of SEQ ID NO: 5; and functional variants of PtPRG5 and homologs of PtPRG5 having an amino acid sequence with at least 59% sequence identity to SEQ ID NO: 5.

36. A method of producing a transgenic plant comprising:
introducing into a plant cell an exogenous nucleic acid that encodes a proton gradient regulation 5 (PGR5) polypeptide;
expressing the PGR5 polypeptide in the cell; and
cultivating the cell to generate a plant, wherein the transformed plant has increased tolerance, relative to a corresponding wild-type plant, to one or more conditions selected from: high light, water-deficit, and drought.

37. The A method of producing a transgenic plant of claim 36,
wherein the PGR5 polypeptide is selected from: an *Arabidopsis thaliana* PGR5 (AtPRG5) polypeptide having the amino acid sequence of SEQ ID NO: 3; functional variants of AtPRG5 and homologs of AtPRG5 having an amino acid sequence with at least 59% sequence identity to SEQ ID NO: 3; a *Pinus taeda* PGR5 (PtPGR5) polypeptide having the amino acid sequence of SEQ ID NO: 5; and functional variants of PtPRG5 and homologs of PtPRG5 having an amino acid sequence with at least 59% sequence identity to SEQ ID NO: 5.

38. The transformed plant cell of claim 3, wherein the AtPRG5 polypeptide has the amino acid sequence of SEQ ID NO: 3.

39. The transformed plant cell of claim 3, wherein the PtPGR5 polypeptide has an the amino acid sequence of SEQ ID NO: 5.

* * * * *

SEQUENCE LISTING

<160> NUMBER OF SEQ ID NOS: 5

<210> SEQ ID NO 1
<211> LENGTH: 1100
<212> TYPE: DNA
<213> ORGANISM: Arabidopsis thaliana

<400> SEQUENCE: 1

```
atctgttaca gattattact gtacaatcca gcaaaaacta ggcctgggat ttcggattaa      60
cccaatgacc gaactgaaca aaccgttttt ttggttctga taaccgacta tgaagggaag     120
gctaaaccga tcggcgaaat tataattgaa gttcggttct cggttcggca gacataaccg     180
atcagttttc tcggttaata gatactataa atataaagat aaaaacatta gatctaatct     240
ttttagcttc ttctccgttt cctttttgatc ctcatccatg gctatttagt caattctctc     300
tatctgcatg tggttttcac tatggtagca cgtcggggca tatttcgtta cggagatatc     360
gtcatccctc gctatcaccg tcaccgtcac agacgtagat ctgctgatta tgaagagggt     420
agcggcacca agataccatc aaccctaatt tttaataggt ttggattttt agttattttg     480
ggtttaagtt tgttttttcgt tttggcccaa ttattggttt gtaattataa aattttgttt     540
atcttcgccc attctataat ttttgttttg acccattatc ttgatttttgg acttattcgg     600
tataaactaa ccgaactaaa aaaaaaatcg gtttagttca gagttgattt tgaatcctat     660
aaccaaaccg acccgaacca aatctttatt cggtttaatt tgacaaaatt ttaaagaacc     720
gaaaaaaccg attaaaccaa accgaaccga ttacccgaat aaaccgaatg cccaggccaa     780
aaacaactga aaataaaaaa taaaaatga gataggagaa tatttaatcc gacggtggag     840
aaatgttgat ataataaaac gtgatacaga ggatcataaa cccgcaacat gagaaacgta     900
ataagttaag tcaaaaaaac gaaaaagcca gaatcatatt tgtggctctg gtttctccat     960
ccaaacaaaa acaacaccca aaccttgtcc acaccaaaat gttaaactca aaatccaacc    1020
acacacacac aatttctctt cctctctacc attaacatcg atcagaaaga ccgagagaga    1080
gagggagaag ctgattgatt                                                 1100
```

<210> SEQ ID NO 2
<211> LENGTH: 402
<212> TYPE: DNA
<213> ORGANISM: Arabidopsis thaliana

<400> SEQUENCE: 2

```
atggctgctg cttcgatttc tgcaatagga tgtaatcaaa ctttgatagg aacttccttc      60
tatggaggat ggggaagttc catctccgga gaagattacc aaaccatgct ctccaagaca     120
gttgcgccac cgcaacaagc cagagtctca aggaaagcaa tcagagcagt tccaatgatg     180
aagaatgtca atgaaggcaa aggcttattt gcacctctag ttgttgtcac acgcaaccta     240
gtaggcaaga agaggtttaa tcagctcaga ggaaaagcca ttgccttaca ctctcaggtg     300
atcactgagt tttgcaaatc gattggagca gatgcaaaac agagacaagg gcttatcagg     360
cttgctaaga agaatggaga gaggcttggt ttccttgctt ag                        402
```

<210> SEQ ID NO 3
<211> LENGTH: 133

```
<212> TYPE: PRT
<213> ORGANISM: Arabidopsis thaliana

<400> SEQUENCE: 3

Met Ala Ala Ala Ser Ile Ser Ala Ile Gly Cys Asn Gln Thr Leu Ile
1               5                   10                  15

Gly Thr Ser Phe Tyr Gly Gly Trp Gly Ser Ser Ile Ser Gly Glu Asp
            20                  25                  30

Tyr Gln Thr Met Leu Ser Lys Thr Val Ala Pro Pro Gln Gln Ala Arg
        35                  40                  45

Val Ser Arg Lys Ala Ile Arg Ala Val Pro Met Met Lys Asn Val Asn
    50                  55                  60

Glu Gly Lys Gly Leu Phe Ala Pro Leu Val Val Thr Arg Asn Leu
65                  70                  75                  80

Val Gly Lys Lys Arg Phe Asn Gln Leu Arg Gly Lys Ala Ile Ala Leu
                85                  90                  95

His Ser Gln Val Ile Thr Glu Phe Cys Lys Ser Ile Gly Ala Asp Ala
            100                 105                 110

Lys Gln Arg Gln Gly Leu Ile Arg Leu Ala Lys Lys Asn Gly Glu Arg
        115                 120                 125

Leu Gly Phe Leu Ala
    130

<210> SEQ ID NO 4
<211> LENGTH: 402
<212> TYPE: DNA
<213> ORGANISM: Pinus taeda

<400> SEQUENCE: 4
atggctacaa tttccagcat accagcagca gggaacaacg tgctgcggcg tggaatgact      60
attaatgatg ggagcgggtg gaagaagtct tccatggcgg gggatggttc cgctcaactg     120
aatgcgcgcc tatggtctta caggacgtcg ggcaaggccg ttcgagctca gcctgtaatg     180
ggcaataaaa atgaaggaaa aggactattc gctcctctgg tggtgctcgc tcgcaatatc     240
atcggcaaaa aaccccttcaa ccaattgaga ggaaaagcta ttgccttgca ctcacaggtt    300
attacggaat tttgcaaatc cataggagct gatgccaaac aaagacaagg cttgattcgt     360
ttggctaaga aaatggtgaa aagttggggg ttcttggcgt ag                        402

<210> SEQ ID NO 5
<211> LENGTH: 133
<212> TYPE: PRT
<213> ORGANISM: Pinus taeda

<400> SEQUENCE: 5

Met Ala Thr Ile Ser Ser Ile Pro Ala Ala Gly Asn Asn Val Leu Arg
1               5                   10                  15

Arg Gly Met Thr Ile Asn Asp Gly Ser Gly Trp Lys Lys Ser Ser Met
            20                  25                  30

Ala Gly Asp Gly Ser Ala Gln Leu Asn Ala Arg Leu Trp Ser Tyr Arg
        35                  40                  45

Thr Ser Gly Lys Ala Val Arg Ala Gln Pro Val Met Gly Asn Lys Asn
    50                  55                  60

Glu Gly Lys Gly Leu Phe Ala Pro Leu Val Val Leu Ala Arg Asn Ile
65                  70                  75                  80

Ile Gly Lys Lys Pro Phe Asn Gln Leu Arg Gly Lys Ala Ile Ala Leu
                85                  90                  95
```

-continued

```
His Ser Gln Val Ile Thr Glu Phe Cys Lys Ser Ile Gly Ala Asp Ala
            100                 105                 110

Lys Gln Arg Gln Gly Leu Ile Arg Leu Ala Lys Lys Asn Gly Glu Lys
        115                 120                 125

Leu Gly Phe Leu Ala
    130
```